United States Patent
Dax et al.

(10) Patent No.: US 11,091,473 B2
(45) Date of Patent: Aug. 17, 2021

(54) COMPOUNDS FOR PAIN TREATMENT, COMPOSITIONS COMPRISING SAME, AND METHODS OF USING SAME

(71) Applicant: ACADIA PHARMACEUTICALS INC., San Diego, CA (US)

(72) Inventors: Scott L. Dax, Landenberg, PA (US); Pasquale N. Confalone, Wilmington, DE (US)

(73) Assignee: Acadia Pharmaceuticals Inc., San Diego, CA (US)

( * ) Notice: Subject to any disclaimer, the term of this patent is extended or adjusted under 35 U.S.C. 154(b) by 0 days.

(21) Appl. No.: 16/417,300

(22) Filed: May 20, 2019

(65) Prior Publication Data

US 2019/0367499 A1     Dec. 5, 2019

Related U.S. Application Data

(60) Provisional application No. 62/677,496, filed on May 29, 2018.

(51) Int. Cl.
| | | |
|---|---|---|
| *C07D 413/12* | (2006.01) | |
| *C07D 417/12* | (2006.01) | |
| *A61P 25/04* | (2006.01) | |

(52) U.S. Cl.
CPC ............ *C07D 417/12* (2013.01); *A61P 25/04* (2018.01)

(58) Field of Classification Search
CPC .................................................. C07D 417/12
USPC ........................................ 546/270.7; 514/342
See application file for complete search history.

(56) References Cited

U.S. PATENT DOCUMENTS

| | | | |
|---|---|---|---|
| 4,785,008 | A | 11/1988 | Coquelet et al. |
| 5,840,739 | A | 11/1998 | Bergeron |
| 9,102,636 | B2 | 8/2015 | Mannion et al. |
| 2004/0242494 | A1 | 12/2004 | Brenchley et al. |

FOREIGN PATENT DOCUMENTS

| | | |
|---|---|---|
| EP | 2498752 A2 | 9/2012 |
| EP | 3070084 A1 | 9/2016 |
| WO | 2006114274 A1 | 11/2006 |
| WO | 2008054292 A1 | 5/2008 |
| WO | 2011059324 A2 | 5/2011 |
| WO | 2011112602 A1 | 9/2011 |
| WO | 2018102726 A1 | 6/2018 |

OTHER PUBLICATIONS

Esumi et al, "Metabolic fate, etc.," CA 120:260452 (Year: 1994).*
Yu et al., "Physical characterization of, etc.," PSTT, vl. 1(3), 118-127). (Year: 1998).*
Braga et al., "Making crystals from . . . " J. Royal Soc. Chem. Commun. p. 3635-3645. (Year: 2005).*
Bernstein, "Polymorphism in . . . " p. 115-118, 272. (Year: 2002).*
Davidovich et al., "Detection of polymorphism . . . " Am. Pharm. Rev. v.&(1) p. 10, 12, 14, 16, 100). (Year: 2004).*
Dean "Analytical Chem . . . " p. 10.24-10.26. (Year: 1995).*
Ivanisevic et al. "Use of X-ray . . . " Pharm. Sci. Encycl. p. 1-42. (Year: 2010).*
Seddon "Pseudopolymorph . . . " Crystal Growth & design v.4(6) p. 108 (2 pages from internet) (Year: 2004).*
Jain et al., "Polymorphism in Pharmacy", Indian Drugs 23(6) 315-329. (Year: 1986).*
Jordan "Tamoxifen . . . " Nature Rev. v.2. p. 205-213. (Year: 2003).*
Kirk-Othmer Encyclopedia of Chemical Technology, 8, pp. 95-147. (Year: 2002).*
Vippagunta et al., "Crystalline Solids", Advanced Drug Delivery Reviews 48 3-26, (Year: 2001).*
Guillory (in Brittain ed.), "Polymorphism in Pharmaceutical Solids.," NY: Marcel Dekker, Inc., 1-2, 125-181, 183-226. (Year: 1999).*
PCT International Search Report & Written Opinion dated Jul. 23, 2019 for PCT International Application No. PCT/US2019/033140.
Rothweiler, et al., "Luciferin and derivatives as a DYRK selective scaffold for the design of protein kinase inhibitors", European Journal of Medicinal Chemistry, vol. 94, Feb. 25, 2015, pp. 340-348.
International Search Report dated Apr. 21, 2020 for related PCT Application No. PCT/US2019/067454.

* cited by examiner

*Primary Examiner* — Patricia L Morris
(74) *Attorney, Agent, or Firm* — Saul Ewing Arnstein & Lehr LLP; Domingos J. Silva; Dennis Ostrovsky

(57) ABSTRACT

The invention relates to compounds of formula (I), compositions containing the same, and methods for treating and/or diminishing pain in a subject in need thereof. The compounds of formula (I) are effective for treating opioid-induced tachyphylaxis and opioid-induced hyperalgesia.

7 Claims, No Drawings

COMPOUNDS FOR PAIN TREATMENT, COMPOSITIONS COMPRISING SAME, AND METHODS OF USING SAME

CROSS-REFERENCE TO RELATED APPLICATION

This application claims priority to U.S. Provisional Patent Application Ser. No. 62/677,496 entitled "COMPOUNDS FOR PAIN TREATMENT, COMPOSITIONS COMPRISING SAME, AND METHODS OF USING SAME," filed May 29, 2018, the disclosure of which is incorporated herein by reference in its entirety.

BACKGROUND OF THE INVENTION

Pain is defined as an unpleasant sensory and emotional experience. Pain, however, can be informative and useful. For example, nociceptive pain is often indicative of injury (e.g., tissue damage), and such pain typically evokes escape or protective behaviors in animals or in a human, in order to remove itself, or protect itself, from further exposure to the insult. However, inflammation, cellular and neuronal damage and other processes resulting from injury or disease can lead to states of chronic pathological pain. Hyperalgesia is a condition in which enhanced sensitivity to noxious stimuli is present and thus the perception of pain is exaggerated. Allodynia is a condition in which normally non-noxious stimuli become painful. Persistent or chronic pain, manifested as hyperalgesia and/or allodynia, remains challenging to treat. Many patients do not respond to existing therapeutics, or have their pain poorly managed (i.e., inadequate relief), or experience relief of an inadequate duration.

Chronic pain contributes to over $600 billion worth of healthcare expenditures annually, more than the yearly cost of cancer, heart disease, and diabetes combined. Neuropathic pain affects between 6 and 10% of the population and is associated with decreased quality of life and socioeconomic burdens exceeding all other chronic pain disorders. A recent meta-analysis of more than 200 neuropathic pain clinical trials indicates that the "number needed to treat" (the average number of patients who need to be treated to prevent one additional bad outcome; e.g., the number of patients that need to be treated for one of them to benefit compared with a control in a clinical trial) to achieve even 50% pain relief in this population is between 4 and 10. This astonishing lack of efficacy has a profound influence on patient quality of life and is a source of frustration for caregivers. Many existing neuropathic pain therapeutics either have unknown mechanisms or are thought to reduce pain by reducing neuronal excitability. To develop the next generation of neuropathic pain therapeutics, new, mechanism-based agents that target specific pathways that lead to aberrant neuronal signaling must be developed.

The administration of opioids to treat pain is a well-recognized and commonly employed therapy in medicine. Unfortunately, tolerance to opioids (tachyphylaxis) and opioid-induced hyperalgesia can often result during the course of therapy. In such patients, increasingly higher doses of opioids are needed to provide an acceptable level of pain relief and, in doing so, the patient is thereby subjected to adverse side effects and safety concerns that are characteristic of opioids. These include respiratory depression, constipation, nausea and vomiting. Such patients are likewise more likely to develop dependence on opioids, suffer opioid withdrawal on discontinuation of treatment, and may be more susceptible to engage in abuse of these medications.

Tachyphylaxis is a phenomenon in which the repeated administration of a drug such as a narcotic analgesic results in a rapidly appearing and marked decrease in the effectiveness of that drug. In opioid-induced hyperalgesia, prolonged administration of opioids also results in a paradoxical increase in pain, or a hypersensitivity to a stimulus that is thought to be unrelated to the original injury or insult. Opioid-induced tachyphylaxis and opioid-induced hyperalgesia have been well documented in animal models of nociception as well as in human clinical trials. These phenomena present significant clinical challenges for the treatment of pain and therefore new compounds, which do not act through opioid mechanisms, are needed to treat pain and/or to alleviate hyperalgesia and tolerance.

Endogenous reactive species produced by injury, irritant and disease are key drivers of pain, as can be demonstrated in animal models of hyperalgesia and allodynia. Reactive oxygen species (ROS) and reactive nitrogen species (RNS) include free radicals such as superoxide and hydroxyl radical as well as the powerful oxidants peroxynitrite (OONO$^-$), and (hydrogen) peroxide ($H_2O_2$). Both peroxynitrite (PN) and hydrogen peroxide, generated in the periphery after injury, contribute to changes in excitability in sensory afferents.

Peroxynitrite has been implicated in the development of opiate-induced antinociceptive (pain) tolerance (tachyphylaxis). Peroxynitrite results from the diffusion-controlled reaction of superoxide ($O_2^-$) and nitric oxide (.NO). Unlike other endogenously produced reactive species/oxidants, peroxynitrite is not managed by enzymatic control. Peroxynitrite formation is facile, unleashing its powerful oxidative properties essentially unchecked, causing downstream effects that can cause pain.

In contrast, superoxide is formed from the action of NADPH oxidases and xanthine oxidase, and nitric oxide is produced by nitric oxide synthases (NOS). Hydrogen peroxide is formed from superoxide and the action of superoxide dismutase. During cellular stress (such as, for example, inflammation, nerve injury, ischemia), the action of these enzymatic systems can cause nitric oxide, superoxide and peroxide levels to increase significantly, which can lead to neuronal damage, hyperalgesia and allodynia. Concomitant increases in nitric oxide and superoxide can lead to greatly increased localized increases in peroxynitrite, which is capable of nitrating tyrosine residues and cross-linking cysteine residues within proteins, causing ion channel hyper-excitability (such as that of TRPA1 and $Na_{V1.8}$) and disrupting glutathione-disulfide homeostastis. Collectively, these effects lead to neuronal sensitization and pain. Thus there exists a need for new compounds, new methods and new inventions that decrease the level or activity of reactive nitrogen species (RNS) and reactive oxygen species (ROS), such as peroxynitrite and peroxide.

There is thus a need for novel compounds and methods that can be used to treat pain. This invention addresses this unmet need.

BRIEF SUMMARY OF THE INVENTION

Provided herein are compounds of formula (I), or a salt, solvate, enantiomer, diastereoisomer or tautomer thereof:

(I)

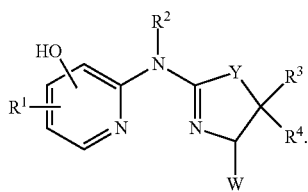

(Ia)

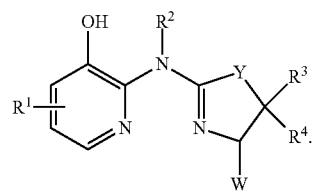

Administration of compounds of formula (I), in various embodiments, decreases the level or activity of reactive nitrogen species (RNS) and reactive oxygen species (ROS), such as peroxynitrite and peroxide in a subject's body. The compounds of formula (I), in some embodiments, are effective for treating opioid-induced tachyphylaxis and opioid-induced hyperalgesia.

DETAILED DESCRIPTION OF THE INVENTION

The present invention provides compounds that can be used to treat pain. In certain embodiments, the compounds of the invention reduce hyperalgesia and/or allodynia.

Compounds and Compositions

The invention includes a compound of formula (I), or a salt, solvate, enantiomer, diastereoisomer or tautomer thereof:

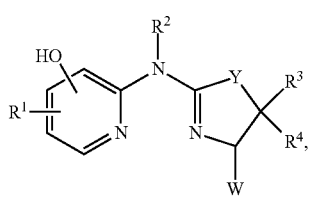

(I)

wherein in (I):

Y is selected from the group consisting of S, O, NH, NR, and $CH_2$;

$R^1$ is selected from the group consisting of H, $C_1$-$C_6$ alkyl, $C_3$-$C_8$ cycloalkyl, $C_1$-$C_6$ alkenyl, $C_1$-$C_6$ alkynyl, aryl, arylalkyl, heteroarylalkyl, and heteroaryl, wherein the alkyl, cycloalkyl, alkenyl, alkynyl, aryl (such as phenyl), arylalkyl (such as phenylalkyl), heteroarylalkyl, or heteroaryl group is independently optionally substituted;

$R^2$ is selected from the group consisting of H, —C(=O)H, —C(=O)R, and —$CH_2$OR;

$R^3$ and $R^4$ are independently selected from the group consisting of H and optionally substituted $C_1$-$C_6$ alkyl, or $R^3$ and $R^4$ can combine to form $C_1$-$C_6$ alkylene;

W is selected from the group consisting of H, $C_1$-$C_6$ alkyl, $C_3$-$C_8$ cycloalkyl, $C_1$-$C_6$ alkoxy, $C_1$-$C_6$ hydroxyalkyl, —CHO, —C(=O)OR, —C(=O)NRR, cyano, hydroxy, aryl, and heteroaryl, wherein the alkyl, alkoxy, cycloalkyl, aryl, or heteroaryl group is independently optionally substituted, and wherein each occurrence of R is independently H, $C_1$-$C_6$ alkyl, and $C_3$-$C_8$ cycloalkyl; and each occurrence of R is independently selected from the group consisting of $C_1$-$C_6$ alkyl and $C_3$-$C_8$ cycloalkyl In certain embodiments, the compound of formula (I) is a compound of formula (Ia), or a salt, solvate, enantiomer, diastereoisomer or tautomer thereof:

In certain embodiments, Y is S. In other embodiments, Y is O. In yet other embodiments, Y is NH. In yet other embodiments, Y is NR. In yet other embodiments, Y is $CH_2$.

In certain embodiments, $R^2$ is H.

In certain embodiments, Y is S; and $R^2$ is H.

In certain embodiments, W is selected from the group consisting of H, $C_1$-$C_6$ hydroxyalkyl, —CHO, —C(=O)OR, and —C(=O)NRR, wherein the alkyl, alkoxy, cycloalkyl, aryl, or heteroaryl group is independently optionally substituted and wherein each occurrence of R is independently H, $C_1$-$C_6$ alkyl, and $C_3$-$C_8$ cycloalkyl.

In certain embodiments, Y is S; $R^2$ is H; and W is selected from the group consisting of H, $C_1$-$C_6$ hydroxyalkyl, —CHO, —C(=O)OR, and —C(=O)NRR, wherein the alkyl, alkoxy, cycloalkyl, aryl, or heteroaryl group is independently optionally substituted and wherein each occurrence of R is independently H, $C_1$-$C_6$ alkyl, and $C_3$-$C_8$ cycloalkyl.

In certain embodiments, $R^3$ and $R^4$ are independently selected from the group consisting of H and $C_1$-$C_6$ alkyl.

In certain embodiments, Y is S; $R^2$ is H; W is selected from the group consisting of H, $C_1$-$C_6$ hydroxyalkyl, —CHO, —C(=O)OR, and —C(=O)NRR, wherein the alkyl, alkoxy, cycloalkyl, aryl, or heteroaryl group is independently optionally substituted and wherein each occurrence of R is independently H, $C_1$-$C_6$ alkyl, and $C_3$-$C_8$ cycloalkyl; and $R^3$ and $R^4$ are independently selected from the group consisting of H and $C_1$-$C_6$ alkyl.

In certain embodiments, the compound of the invention is at least one selected from the group consisting of:
(R)-2-(3-Hydroxy-pyridin-2-ylamino)-5,5-dimethyl-4,5-dihydro-thiazole-4-carboxylic acid;
(S)-2-(3-Hydroxy-pyridin-2-ylamino)-5,5-dimethyl-4,5-dihydro-thiazole-4-carboxylic acid;
(R)-2-((3-hydroxypyridin-2-yl)amino)-4,5-dihydrothiazole-4-carboxylic acid;
(S)-2-((3-hydroxypyridin-2-yl)amino)-4,5-dihydrothiazole-4-carboxylic acid;
or a salt, solvate, enantiomer, diastereoisomer or tautomer thereof.

The invention relates to compounds, compositions and methods for diminishing pain in a subject in need thereof.

In certain embodiments, the compounds described herein cause destruction of reactive nitrogen species (RNS), such as peroxynitrite, and/or reactive oxygen species (ROS), such as (hydrogen) peroxide.

In certain embodiments, the compounds described herein decompose reactive nitrogen species (RNS), such as peroxynitrite, and/or reactive oxygen species (ROS), such as (hydrogen) peroxide.

In certain embodiments, the compounds described herein react with reactive nitrogen species (RNS), such as peroxynitrite, and/or reactive oxygen species (ROS), such as (hydrogen) peroxide.

In certain embodiments, the compounds described herein reduce levels of, and/or inhibit the activity of, reactive nitrogen species (RNS), such as peroxynitrite, and/or reduce levels, and/or inhibit the activity, of reactive oxygen species (ROS), such as (hydrogen) peroxide.

In certain embodiments, the compounds described herein cause destruction of reactive nitrogen species, such as peroxynitrite.

In certain embodiments, the compounds described herein cause destruction of reactive oxygen species, such as (hydrogen) peroxide.

In certain embodiments, the compounds described herein decompose reactive nitrogen species, such as peroxynitrite.

In certain embodiments, the compounds described herein decompose reactive oxygen species, such as (hydrogen) peroxide.

In certain embodiments, the compounds described herein react with reactive nitrogen species, such as peroxynitrite.

In certain embodiments, the compounds described herein react with reactive oxygen species, such as (hydrogen) peroxide.

In certain embodiments, the compounds described herein reduce levels, or inhibit activity, of reactive nitrogen species, such as peroxynitrite.

In certain embodiments, the compounds described herein diminish levels, or inhibit activity, of reactive oxygen species such as (hydrogen) peroxide.

In certain embodiments, the present invention provides a method of administering a compound of the invention to provide pain relief.

In certain embodiments, the present invention provides compounds, compositions and methods for reducing or abolishing chronic pain in a subject in need thereof.

In certain embodiments, the present invention provides compounds, compositions and methods for reducing or abolishing hyperalgesia in a subject in need thereof.

In certain embodiments, the present invention provides compounds, compositions and methods for reducing or abolishing allodynia in a subject in need thereof.

In certain embodiments, the present invention provides compounds, compositions and methods for reducing or abolishing spontaneous pain in a subject in need thereof.

In certain embodiments, the present invention provides compounds, compositions and methods for reducing or abolishing pain arising from surgical procedures, in a subject in need thereof.

In certain embodiments, the present invention provides compounds, compositions and methods for reducing or abolishing neuropathic pain, such as that arising from diabetes, in a subject in need thereof.

In other embodiments, the invention relates to compounds, compositions and methods for reducing or abolishing neuropathic pain, such as that arising from cancer, chemotherapy or cancer radiation therapy, in a subject in need thereof.

Certain phenolic compounds with analgesic properties were previously disclosed in U.S. Pat. No. 9,102,636 B2, U.S. Patent Application Publications No. US20110224269 A1 and No. US20120202860 A1, and PCT Application Publication No. WO2011112602 A1, each of which is hereby incorporated by reference in its entirety.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in animal pharmacology, pharmaceutical science, separation science, and organic chemistry are those well-known and commonly employed in the art.

As used herein, the articles "a" and "an" refer to one or to more than one (i.e. to at least one) of the grammatical object of the article. By way of example, "an element" means one element or more than one element.

As used herein, the term "about" is understood by persons of ordinary skill in the art and varies to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

In one aspect, the terms "co-administered" and "co-administration" as relating to a subject refer to administering to the subject a compound of the invention or salt thereof along with a compound that may also treat diseases and/or disorders contemplated herein. In certain embodiments, the co-administered compounds are administered separately, or in any kind of combination as part of a single therapeutic approach. The co-administered compound may be formulated in any kind of combinations as mixtures of solids and liquids under a variety of solid, gel, and liquid formulations, and as a solution.

As used herein, the term "CYP450" as applied to enzymes refers to cytochrome P450 family of enzymes.

As used herein, a "disease" is a state of health of a subject wherein the subject cannot maintain homeostasis, and wherein if the disease is not ameliorated then the subject's health continues to deteriorate.

As used herein, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

As used herein, the term "$ED_{50}$" refers to the effective dose of a formulation that produces 50% of the maximal effect in subjects that are administered that formulation.

As used herein, an "effective amount," "therapeutically effective amount" or "pharmaceutically effective amount" of a compound is that amount of compound that is sufficient to provide a beneficial effect to the subject to which the compound is administered.

"Instructional material," as that term is used herein, includes a publication, a recording, a diagram, or any other medium of expression that can be used to communicate the usefulness of the composition and/or compound of the invention in a kit. The instructional material of the kit may, for example, be affixed to a container that contains the compound and/or composition of the invention or be shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

As used herein, the term "pharmaceutical composition" or "composition" refers to a mixture of at least one compound useful within the invention with a pharmaceutically acceptable carrier. The pharmaceutical composition facilitates administration of the compound to a subject.

As used herein, the term "pharmaceutically acceptable" refers to a material, such as a carrier or diluent, which does not abrogate the biological activity or properties of the compound useful within the invention, and is relatively non-toxic, i.e., the material may be administered to a subject without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the subject such that it may perform its intended function. Typically, such constructs are carried or transported from one organ, or portion of the body, to another organ, or portion of the body.

Each carrier must be "acceptable" in the sense of being compatible with the other ingredients of the formulation, including the compound useful within the invention, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the subject. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof.

The term "prevent," "preventing" or "prevention," as used herein, means avoiding or delaying the onset of symptoms associated with a disease or condition in a subject that has not developed such symptoms at the time the administering of an agent or compound commences. Disease, condition and disorder are used interchangeably herein.

By the term "specifically bind" or "specifically binds," as used herein, is meant that a first molecule preferentially binds to a second molecule (e.g., a particular receptor or enzyme), but does not necessarily bind only to that second molecule.

As used herein, a "subject" may be a human or non-human mammal or a bird. Non-human mammals include, for example, livestock and pets, such as ovine, bovine, porcine, canine, feline and murine mammals. Preferably, the subject is human.

The term "treat," "treating" or "treatment," as used herein, means reducing the frequency or severity with which symptoms of a disease or condition are experienced by a subject by virtue of administering an agent or compound to the subject.

As used herein, the term "alkyl," by itself or as part of another substituent means, unless otherwise stated, a straight or branched chain hydrocarbon having the number of carbon atoms designated (i.e., $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$) alkyl, such as, but not limited to, ethyl, methyl, isopropyl, isobutyl, n-pentyl, n-hexyl and cyclopropylmethyl.

As used herein, the term "alkylene" by itself or as part of another substituent means, unless otherwise stated, a straight or branched hydrocarbon group having the number of carbon atoms designated (i.e., $C_1$-$C_{10}$ means one to ten carbon atoms) and includes straight, branched chain, or cyclic substituent groups, wherein the group has two open valencies. Examples include methylene, 1,2-ethylene, 1,1-ethylene, 1,1-propylene, 1,2-propylene and 1,3-propylene.

As used herein, the term "cycloalkyl," by itself or as part of another substituent means, unless otherwise stated, a cyclic chain hydrocarbon having the number of carbon atoms designated (i.e., $C_3$-$C_6$ means a cyclic group comprising a ring group consisting of three to six carbon atoms) and includes straight, branched chain or cyclic substituent groups. Examples include cyclopropyl, cyclobutyl, cyclopentyl, cyclohexyl, cycloheptyl, and cyclooctyl. Most preferred is ($C_3$-$C_6$)cycloalkyl, such as, but not limited to, cyclopropyl, cyclobutyl, cyclopentyl and cyclohexyl.

As used herein, the term "alkenyl," employed alone or in combination with other terms, means, unless otherwise stated, a stable mono-unsaturated or di-unsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —$CH_2$—CH=$CH_2$.

As used herein, the term "alkynyl," employed alone or in combination with other terms, means, unless otherwise stated, a stable straight chain or branched chain hydrocarbon group with a triple carbon-carbon bond, having the stated number of carbon atoms. Non-limiting examples include ethynyl and propynyl, and the higher homologs and isomers. The term "propargylic" refers to a group exemplified by —$CH_2$—C≡CH. The term "homopropargylic" refers to a group exemplified by —$CH_2CH_2$—C≡CH. The term "substituted propargylic" refers to a group exemplified by —$CR_2$—C≡CR, wherein each occurrence of R is independently H, alkyl, substituted alkyl, alkenyl or substituted alkenyl, with the proviso that at least one R group is not hydrogen. The term "substituted homopropargylic" refers to a group exemplified by —CR$_2$CR$_2$—C≡CR, wherein each occurrence of R is independently H, alkyl, substituted alkyl, alkenyl or substituted alkenyl, with the proviso that at least one R group is not hydrogen.

As used herein, the term "substituted alkyl," "substituted cycloalkyl," "substituted alkenyl" or "substituted alkynyl" means alkyl, cycloalkyl, alkenyl or alkynyl, as defined above, substituted by one, two or three substituents selected from the group consisting of halogen, alkoxy, tetrahydro-2-H-pyranyl, —NH$_2$, —N(CH$_3$)$_2$, (1-methyl-imidazol-2-yl), pyridin-2-yl, pyridin-3-yl, pyridin-4-yl, —C(=O)OH, trifluoromethyl, —C≡N, —C(=O)O(C$_1$-C$_4$)alkyl, —C(=O)NH$_2$, —C(=O)NH(C$_1$-C$_4$)alkyl, —C(=O)N((C$_1$-C$_4$)alkyl)$_2$, —SO$_2$NH$_2$, —C(=NH)NH$_2$, and —NO$_2$, preferably containing one or two substituents selected from halogen, —OH, alkoxy, —NH$_2$, trifluoromethyl, —N(CH$_3$)$_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl. In certain embodiments, the substituted alkyl is not substituted with a hydroxy group.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are (C$_1$-C$_3$) alkoxy, such as, but not limited to, ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—OH, —CH$_2$—CH$_2$—NH—CH$_3$, —CH$_2$—S—CH$_2$—CH$_3$, and —CH$_2$CH$_2$—S(=O)—CH$_3$. Up to two heteroatoms may be consecutive, such as, for example, —CH$_2$—NH—OCH$_3$, or —CH$_2$—CH$_2$—S—S—CH$_3$.

As used herein, the term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—CH$_3$, —CH=CH—CH$_2$—OH, —CH$_2$—CH=N—OCH$_3$, —CH=CH—N(CH$_3$)—CH$_3$, and —CH$_2$—CH=CH—CH$_2$—SH.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Preferred are phenyl and naphthyl, most preferred is phenyl.

As used herein, the term "aryl-(C$_1$-C$_3$)alkyl" means a functional group wherein a one to three carbon alkylene chain is attached to an aryl group, e.g., —CH$_2$CH$_2$-phenyl or —CH$_2$-phenyl (benzyl). Preferred is aryl-CH$_2$— and aryl-CH(CH$_3$)—. The term "substituted aryl-(C$_1$-C$_3$)alkyl" means an aryl-(C$_1$-C$_3$)alkyl functional group in which the aryl group is substituted. Preferred is substituted aryl (CH$_2$)—. Similarly, the term "heteroaryl-(C$_1$-C$_3$)alkyl" means a functional group wherein a one to three carbon alkylene chain is attached to a heteroaryl group, e.g., —CH$_2$CH$_2$-pyridyl. Preferred is heteroaryl-(CH$_2$)—. The term "substituted heteroaryl-(C$_1$-C$_3$)alkyl" means a heteroaryl-(C$_1$-C$_3$)alkyl functional group in which the heteroaryl group is substituted. Preferred is substituted heteroaryl-(CH$_2$)—.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain embodiments, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (such as, but not limited to, 3-, 4-, 5-, 6- and 7-indolyl), indolinyl, quinolyl, tetrahydroquinolinyl, isoquinolinyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In other embodiments, the substituents vary in number between one and three. In yet other embodiments, the substituents vary in number between one and two. In yet other embodiments, the substituents are independently selected from the group consisting of $C_{1-6}$ alkyl, —OH, $C_{1-6}$ alkoxy, halo, amino, acetamido and nitro. As used herein, where a substituent is an alkyl or alkoxy group, the carbon chain may be branched, straight or cyclic, with straight being preferred.

The following abbreviations are used herein: AcOH, acetic acid; Ar, argon; Boc, butyloxycarbonyl; C, carbon; $CHCl_3$, chloroform; DCM (or $CH_2Cl_2$), methylene chloride (dichloromethane); d, day; DIPEA, N,N-diisopropylethylamine; DMF, N,N-dimethylformamide; DMSO, dimethylsulfoxide; EDTA, ethylene diamine tetraacetic acid; ESI, electrospray ionization; EtOAc, ethyl acetate; GCMS, gas chromatogram-mass spectrometry; h, hour; $H_2$, hydrogen gas; iPrOH, isopropanol; $K_2CO_3$, potassium carbonate; KOH, potassium hydroxide; LCMS, liquid chromatography-mass spectrometry; MeCN or $CH_3CN$, acetonitrile; MEM, methoxyethoxymethyl; MeOH, methanol; $MgSO_4$, magnesium sulfate; MHz, megahertz; min, minute (unit of time); MOM, methoxymethyl; MS, mass spectrometry; $NaHCO_3$, sodium bicarbonate; $Na_2SO_4$, sodium sulfate; NMR, nuclear magnetic resonance; Pd, palladium (metal); Ph, phenyl; PBS, phosphate buffer solution; PE, petroleum ether; PN, peroxynitrite; sec, second (unit of time); SEM, trimethylsilylethoxymethyl; SIN1, 3-morpholino-sydonimine; TEA, trimethylamine; THF, tetrahydrofuran; Tr, trityl (—$CPh_3$); TsCl, tosyl chloride.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Tautomerism

"Tautomers" are structurally distinct isomers that interconvert by tautomerization. "Tautomerization" is a form of isomerization involving the migration of a proton accompanied by changes in bond order, often the interchange of a single bond with an adjacent double bond. Where tautomerization is possible (e.g. in solution), a chemical equilibrium of tautomers can be reached. One well-known example of tautomerization is between a ketone and its corresponding enol. Compounds contemplated within the invention may also undergo tautomerization (to each other) and may exist in anti- or syn-imino-thiazoline forms or as a mixture thereof.

In certain embodiments in which $R^2$=H, the compounds of formula (I) can exist as tautomeric amino-thiazolidine and imino-thiazoline compounds of formulae (IIa), including either or both anti- and syn-regiomers (relative to Y) in the case of imino-thiazoline; or a salt, solvate, enantiomer, diastereoisomer or tautomer thereof:

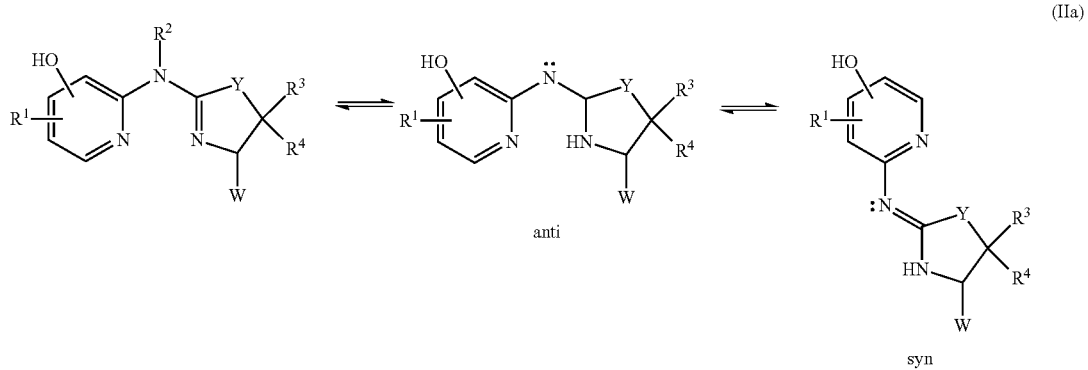

It should be understood that both tautomeric forms of a given compound are contemplated and within the scope of the present invention. Thus, any discussion of any compound disclosed herein should be understood to include both tautomeric forms of that compound, unless otherwise specified.

Acid Addition Salts

Compounds contemplated within the invention can contain a basic nitrogen that can be protonated by a sufficiently strong protic acid. Although any sufficiently strong protic acid may be used, pharmaceutically acceptable acids are preferred so that pharmaceutically-acceptable acid addition salts are formed. "Pharmaceutically acceptable acid" refers to those acids that are not toxic or otherwise biologically undesirable. Pharmaceutically acceptable acid addition salts may be formed with pharmaceutically-acceptable inorganic acids including, but not limited to, hydrochloric acid, hydrobromic acid, sulfuric acid, sulfamic acid, nitric acid, phosphoric acid, and the like.

Pharmaceutically acceptable acid addition salts may also be formed with pharmaceutically acceptable organic acids. Examples of pharmaceutically acceptable organic acids, include but are not limited to, acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, fumaric acid, 2-hydroxyethanesulfonic acid (isethionic acid), lactic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, undecanoic acid, and the like.

Methods of Preparation

Compounds of the invention can be prepared according to the following general schemes. In cases in which the hydroxy substituent is ortho to the carbon-exo-cyclic N bond, a compound of formula (Ia) can be prepared as illustrated in Scheme 1. A 3-hydroxy-2-amino-pyridine (A) is reacted with an alkyl xanthate (such as, but not limited to, potassium ethyl xanthate) to give the cyclized oxazolo[4,5-b]pyridine-2-thiol product (B). Reaction with a chlorinating agent (such as, but not limited to, thionyl chloride) produces a 2-chlorooxazolo[4,5-b]pyridine (C). Subsequent reaction with a penicillamine (W=COOH, $R^3$, $R^4$=CH$_3$), a cysteine (W=COOH, $R^3$, $R^4$=H), or a 2-amino-ethanethiol provides thiazolidine compounds (I) of this invention, which can be converted to an acid addition salt, such as, but not limited to mono-hydrochloride (I-salt), by treatment with an acid.

Scheme 1

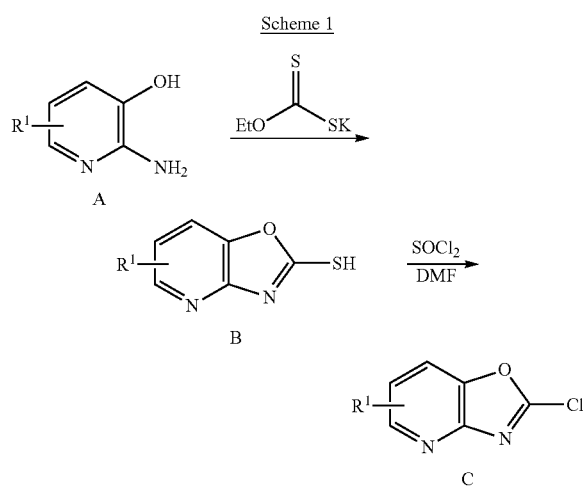

Alternatively, compounds of formula (I) may be prepared as illustrated in Scheme 2. An S-protected 2-amino-ethanethiol (such as, but not limited to, S-trityl-cysteine) is reacted with a 2-chlorooxazolo[4,5-b]pyridine (C) to produce an S-protected 2-aminobenzoxazole (D). Deprotection (such as, but not limited to, detritylation) affords thiazolidine compounds (I) of this invention.

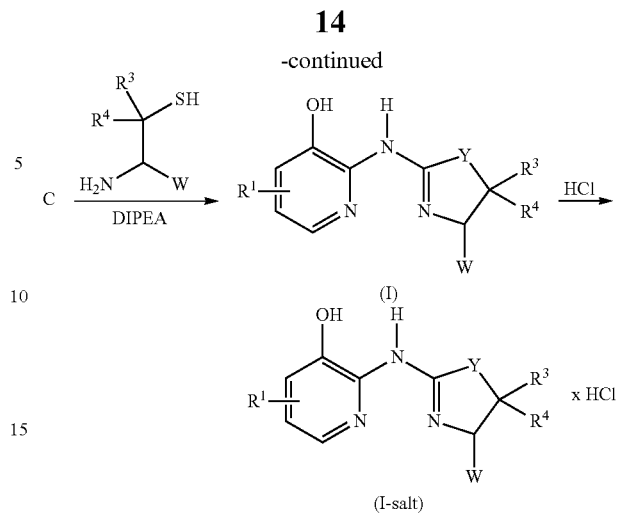

Scheme 2

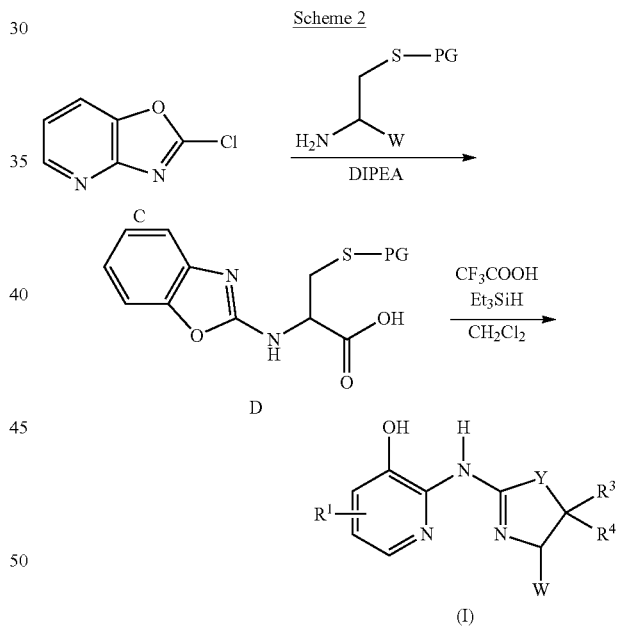

Alternatively, compounds of formula (I) can be prepared as illustrated in Scheme 3. A 3-hydroxy-2-amino-pyridine (A) undergoes protection of the phenolic OH using methodology known to one skilled in the art (e.g., acylation, alkylation (PG=methyl, MOM, MEM, SEM), benzylation, and the like) to give O-protected congener (E), which is subsequently reacted with a cyanating reagent, such as cyanogen bromide, to give cyanamide (F). Reaction of (F) with a penicillamine (W=COOH, $R^3$, $R^4$=CH$_3$), a cysteine (W=COOH, $R^3$, $R^4$=H) or a 2-amino-ethanethiol provides thiazolidine compounds (I) of this invention, which can be converted to an acid addition salt (such as, but not limited to mono-hydrochloride (I-salt) by treatment with an acid.

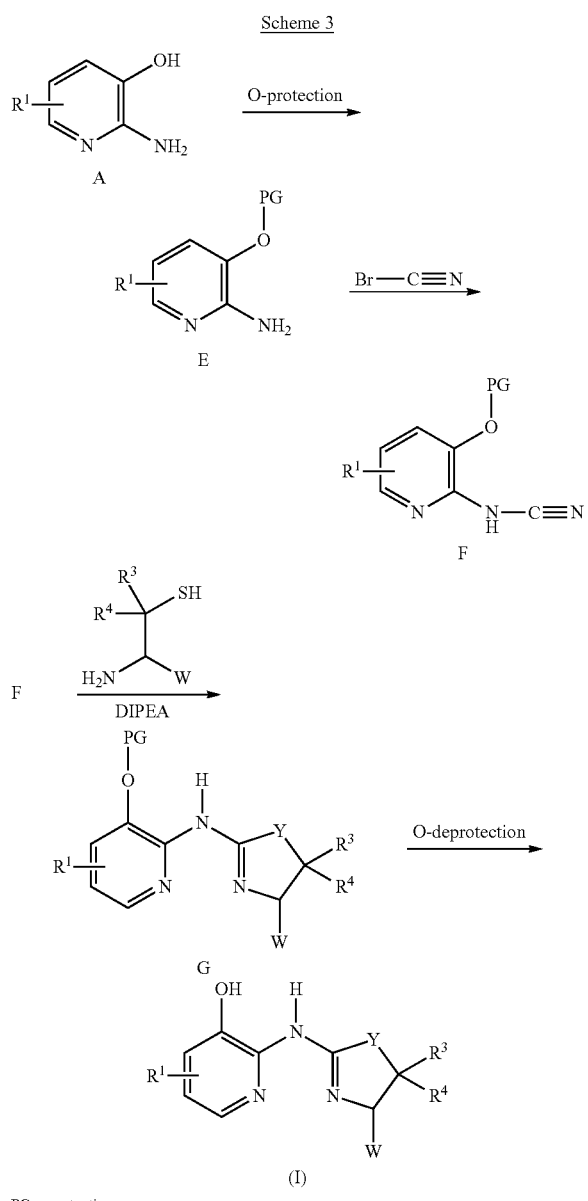

Scheme 3

PG = protecting group

Pharmaceutical Compositions and Formulations

The invention provides pharmaceutical compositions comprising at least one compound of the invention or a salt or solvate thereof, which are useful to practice methods of the invention. Such a pharmaceutical composition may consist of at least one compound of the invention or a salt or solvate thereof, in a form suitable for administration to a subject, or the pharmaceutical composition may comprise at least one compound of the invention or a salt or solvate thereof, and one or more pharmaceutically acceptable carriers, one or more additional ingredients, or some combination of these. At least one compound of the invention may be present in the pharmaceutical composition in the form of a physiologically acceptable salt, such as in combination with a physiologically acceptable cation or anion, as is well known in the art.

In certain embodiments, the pharmaceutical compositions useful for practicing the method of the invention may be administered to deliver a dose of between 1 ng/kg/day and 100 mg/kg/day. In other embodiments, the pharmaceutical compositions useful for practicing the invention may be administered to deliver a dose of between 1 ng/kg/day and 1,000 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for nasal, inhalational, oral, rectal, vaginal, pleural, peritoneal, parenteral, topical, transdermal, pulmonary, intranasal, buccal, ophthalmic, epidural, intrathecal, intravenous or another route of administration. A composition useful within the methods of the invention may be directly administered to the brain, the brainstem, or any other part of the central nervous system of a mammal or bird. Other contemplated formulations include projected nanoparticles, microspheres, liposomal preparations, coated particles, polymer conjugates, resealed erythrocytes containing the active ingredient, and immunologically-based formulations.

In certain embodiments, the compositions of the invention are part of a pharmaceutical matrix, which allows for manipulation of insoluble materials and improvement of the bioavailability thereof, development of controlled or sustained release products, and generation of homogeneous compositions. By way of example, a pharmaceutical matrix may be prepared using hot melt extrusion, solid solutions, solid dispersions, size reduction technologies, molecular complexes (e.g., cyclodextrins, and others), microparticulate, and particle and formulation coating processes. Amorphous or crystalline phases may be used in such processes.

The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology and pharmaceutics. In general, such preparatory methods include the step of bringing the active ingredient into association with a carrier or one or more other accessory ingredients, and then, if necessary or desirable, shaping or packaging the product into a desired single-dose or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In certain embodiments, the compositions of the invention are formulated using one or more pharmaceutically acceptable excipients or carriers. In certain embodiments, the pharmaceutical compositions of the invention comprise a therapeutically effective amount of at least one compound of the invention and a pharmaceutically acceptable carrier. Pharmaceutically acceptable carriers, which are useful, include, but are not limited to, glycerol, water, saline, ethanol, recombinant human albumin (e.g., RECOMBUMIN®), solubilized gelatins (e.g., GELOFUSINE®), and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), recombinant human albumin, solubilized gelatins, suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, isotonic agents, for example, sugars, sodium chloride, or polyalcohols such as mannitol and sorbitol, are included in the composition. Prolonged absorption of the injectable compositions may be brought about by including in the composition an agent that delays absorption, for example, aluminum monostearate or gelatin.

Formulations may be employed in admixtures with conventional excipients, i.e., pharmaceutically acceptable organic or inorganic carrier substances suitable for oral, parenteral, nasal, inhalational, intravenous, subcutaneous, transdermal, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or fragrance-conferring substances and the like. They may also be combined where desired with other active agents, e.g., other analgesic, anxiolytics or hypnotic agents. As used herein, "additional ingredients" include, but are not limited to, one or more ingredients that may be used as a pharmaceutical carrier.

The composition of the invention may comprise a preservative from about 0.005% to 2.0% by total weight of the composition. The preservative is used to prevent spoilage in the case of exposure to contaminants in the environment. Examples of preservatives useful in accordance with the invention include but are not limited to those selected from the group consisting of benzyl alcohol, sorbic acid, parabens, imidurea and combinations thereof. One such preservative is a combination of about 0.5% to 2.0% benzyl alcohol and 0.05% to 0.5% sorbic acid.

The composition may include an antioxidant and a chelating agent which inhibit the degradation of the compound. Antioxidants for some compounds are BHT, BHA, alpha-tocopherol and ascorbic acid in the exemplary range of about 0.01% to 0.3%, or BHT in the range of 0.03% to 0.1% by weight by total weight of the composition. The chelating agent may be present in an amount of from 0.01% to 0.5% by weight by total weight of the composition. Exemplary chelating agents include edetate salts (e.g. disodium edetate) and citric acid in the weight range of about 0.01% to 0.20%, or in the range of 0.02% to 0.10% by weight by total weight of the composition. The chelating agent is useful for chelating metal ions in the composition that may be detrimental to the shelf life of the formulation. While BHT and disodium edetate are exemplary antioxidant and chelating agent, respectively, for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethyl cellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, acacia, and ionic or non ionic surfactants. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as *arachis*, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, ionic and non-ionic surfactants, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying. Methods for mixing components include physical milling, the use of pellets in solid and suspension formulations and mixing in a transdermal patch, as known to those skilled in the art.

Administration/Dosing

The regimen of administration may affect what constitutes an effective amount. The therapeutic formulations may be administered to the patient either prior to or after the onset of a disease or disorder. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, such as a mammal, such as a human, may be carried out using known procedures, at dosages and for periods of time effective to treat a disease or disorder contemplated herein. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 mg/kg to 100 mg/kg of body weight/per day. One of ordinary skill in the art would be able to study the relevant factors and make the determination regarding the effective amount of the therapeutic compound without undue experimentation.

The compound may be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose is readily apparent to the skilled artisan and depends upon a number of factors, such as, but not limited to, type and severity of the disease being treated, and type and age of the animal.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. "Dosage unit form" as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder in a patient.

In certain embodiments, the compositions of the invention are administered to the patient in dosages that range from one to five times per day or more. In other embodiments, the compositions of the invention are administered to the patient in range of dosages that include, but are not limited to, once every day, every two days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physician taking all other factors about the patient into account.

Compounds of the invention for administration may be in the range of from about 1 µg to about 7,500 mg, about 20 µg to about 7,000 mg, about 40 µg to about 6,500 mg, about 80 µg to about 6,000 mg, about 100 µg to about 5,500 mg, about 200 µg to about 5,000 mg, about 400 µg to about 4,000 mg, about 800 µg to about 3,000 mg, about 1 mg to about 2,500 mg, about 2 mg to about 2,000 mg, about 5 mg to about 1,000 mg, about 10 mg to about 750 mg, about 20 mg to about 600 mg, about 30 mg to about 500 mg, about 40 mg to about 400 mg, about 50 mg to about 300 mg, about 60 mg to about 250 mg, about 70 mg to about 200 mg, about 80 mg to about 150 mg, and any and all whole or partial increments there-in-between.

In some embodiments, the dose of a compound of the invention is from about 0.5 µg and about 5,000 mg. In some embodiments, a dose of a compound of the invention used in compositions described herein is less than about 5,000 mg, or less than about 4,000 mg, or less than about 3,000 mg, or less than about 2,000 mg, or less than about 1,000 mg, or less than about 800 mg, or less than about 600 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder in a patient.

The term "container" includes any receptacle for holding the pharmaceutical composition or for managing stability or water uptake. For example, in certain embodiments, the container is the packaging that contains the pharmaceutical composition, such as liquid (solution and suspension), semi-solid, lyophilized solid, solution and powder or lyophilized formulation present in dual chambers. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a disease or disorder in a patient.

Administration

Routes of administration of any of the compositions of the invention include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, epidural, intrapleural, intraperitoneal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, emulsions, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic, generally recognized as safe (GRAS) pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation. Hard capsules comprising the active ingredient may be made using a physiologically degradable composition, such as gelatin. The capsules comprise the active ingredient, and may further comprise additional ingredients including, for example, an inert solid diluent such as calcium carbonate, calcium phosphate, or kaolin.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Injectable formulations may also be prepared, packaged, or sold in devices such as patient-controlled analgesia (PCA) devices. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form in a recombinant human albumin, a fluidized gelatin, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Topical Administration

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (i.e., U.S. Pat. No. 6,323,219). In alternative embodiments, the topically active pharmaceutical composition may be optionally combined with other ingredients such as adjuvants, anti-oxidants, chelating agents, surfactants, foaming agents, wetting agents, emulsifying agents, viscosifiers, buffering agents, preservatives, and the like. In other embodiments, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. For example, it should be present in an amount from about 0.0005% to about 5% of the composition; for example, it should be present in an amount of from about 0.001% to about 1% of the composition. Such compounds may be synthetically- or naturally derived.

Buccal Administration

A pharmaceutical composition of the invention may be prepared, packaged, or sold in a formulation suitable for buccal administration. Such formulations may, for example, be in the form of tablets or lozenges made using conventional methods, and may contain, for example, 0.1 to 20% (w/w) of the active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, may have an average particle or droplet size in the range from about 0.1 to about 200 nanometers, and may further comprise one or more of the additional ingredients described herein. The examples of formulations described herein are not exhaustive and it is understood that the invention includes additional modifications of these and other formulations not described herein, but which are known to those of skill in the art.

Rectal Administration

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

In certain embodiments, the compositions and/or formulations of the present invention may be, but are not limited to, short-term, rapid-offset, as well as controlled, for example, sustained release, delayed release and pulsatile release formulations.

The term "sustained release" is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In certain embodiments of the invention, the compounds useful within the invention are administered to a subject, alone or in combination with another pharmaceutical agent, using a sustained release formulation.

The term "delayed release" is used herein in its conventional sense to refer to a drug formulation that provides for an initial release of the drug after some delay following drug administration and that may, although not necessarily, include a delay of from about 10 minutes up to about 12 hours.

The term "pulsatile release" is used herein in its conventional sense to refer to a drug formulation that provides release of the drug in such a way as to produce pulsed plasma profiles of the drug after drug administration.

The term "immediate release" is used in its conventional sense to refer to a drug formulation that provides for release of the drug immediately after drug administration.

As used herein, "short-term" refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, "rapid-offset" refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

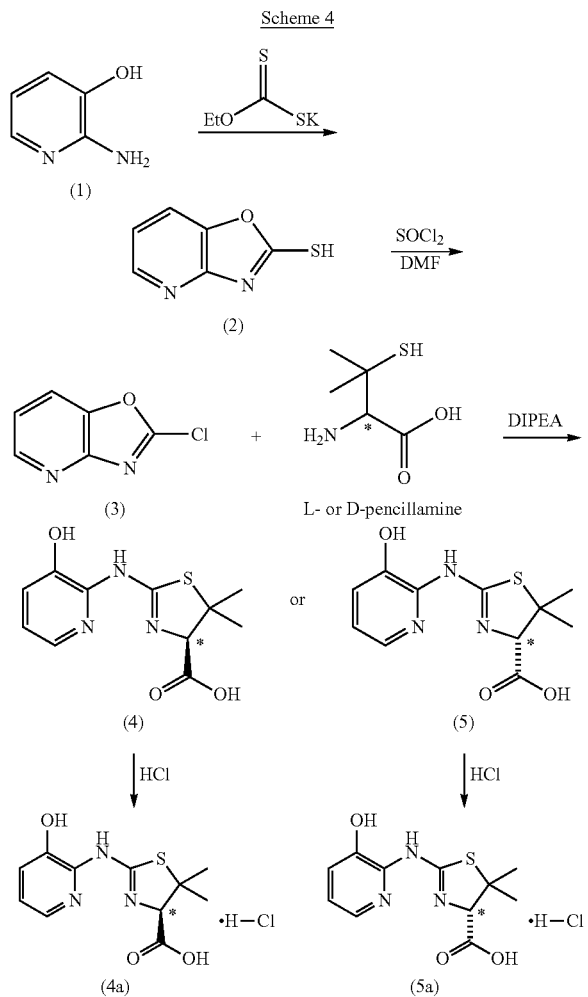

Scheme 4

Example 1: (R)-2-(3-Hydroxy-pyridin-2-ylamino)-5,5-dimethyl-4,5-dihydro-thiazole-4-carboxylic Acid (4) and Corresponding Hydrochloride Salt (4a)

(a) Oxazolo[4,5-b]pyridine-2-thiol (2)

A mixture of 2-amino-pyridin-3-ol (1) (2.00 g, 18.16 mmol) and potassium ethyl xanthate (2.91 g, 18.16 mmol) in ethanol (40 mL) was heated under reflux for 24 h. The solvent was removed in vacuo and water (30 mL) was added. The mixture was acidified with AcOH to pH 5. The resultant precipitate was filtered, washed with water (20 mL) and dried to give oxazolo[4,5-b]pyridine-2-thiol (2) (2.05 g, 74% yield). 300 MHz $^1$H-NMR (DMSO-$d_6$, ppm): 8.21 (dd, J=5.2, 1.3 Hz, 1H) 7.85 (dd, J=8.1, 1.3 Hz, 1H) 7.25 (dd, J=8.1, 5.2 Hz, 1H).

(b) 2-Chloro-oxazolo[4,5-b]pyridine Hydrochloride (3)

A mixture of oxazolo[4,5-b]pyridine-2-thiol (2) (500 mg, 3.29 mmol), thionyl chloride (7 mL) and a catalytic amount of DMF (25 μL) was stirred at room temperature for 4 h. The volatiles were then removed in vacuo. The residue was co-evaporated with toluene (3×20 mL) to give the crude 2-chloro-oxazolo[4,5-b]pyridine hydrochloride (3) (620 mg, quantitative yield), which was used in the next step without purification. 300 MHz $^1$H-NMR (DMSO-$d_6$, ppm): 9.8-8.8 (br s, 1H) 8.02 (dd, J=5.3, 1.3 Hz, 1H) 7.63 (dd, J=7.9, 1.3 Hz, 1H) 7.10 (dd, J=7.9, 5.3 Hz, 1H).

(c) (R)-2-(3-Hydroxy-pyridin-2-ylamino)-5,5-dimethyl-4,5-dihydro-thiazole-4-carboxylic Acid (4)

A solution of 2-chloro-oxazolo[4,5-b]pyridine hydrochloride (3) (346 mg, 1.81 mmol), L-penicillamine (300 mg, 2.01 mmol) and DIPEA (1.74 mL, 10.05 mmol) in THF/MeOH (4/12 mL) was stirred at room temperature for 2 h. The solvent was removed in vacuo. The residue was suspended in water (100 mL) and acidified to pH 3 with 5% $KHSO_4$ solution. The resultant precipitate were filtered, washed with water (100 mL) and diethyl ether (150 mL) to give (R)-2-(3-hydroxy-pyridin-2-ylamino)-5,5-dimethyl-4,5-dihydro-thiazole-4-carboxylic acid (4) (300 mg, 62% yield) as an off-white solid. 300 MHz $^1$H-NMR (DMSO-$d_6$, ppm): 11.0-8.5 (br s, 1H) 7.70 (dd, J=4.8, 1.4 Hz, 1H) 7.06 (dd, J=7.8, 1.4 Hz, 1H) 6.83 (dd, J=7.8, 4.8 Hz, 1H) 4.22 (1H, s) 1.60 (3H, s) 1.37 (3H, s). ESI-MS (m/z): 268 $[M+H]^+$. $[\alpha_D^{20}]$: −129.3 (0.26, methanol).

(d) (R)-2-(3-Hydroxy-pyridin-2-ylamino)-5,5-dimethyl-4,5-dihydro-thiazole-4-carboxylic Acid Hydrochloride (4a)

(R)-2-(3-Hydroxy-pyridin-2-ylamino)-5,5-dimethyl-4,5-dihydro-thiazole-4-carboxylic acid (4) (300 mg, 1.12 mmol) was dissolved in methanol (3 mL) and 4N HCl in 1,4-dioxane (280 μL, 1.12 mmol, 1 eq) was added at 0° C. The mixture was stirred for 30 min, after which time the volatiles were removed in vacuo to give (R)-2-(3-hydroxy-pyridin-2-ylamino)-5,5-dimethyl-4,5-dihydro-thiazole-4-carboxylic acid hydrochloride (4a) (320 mg, 94% yield) as a white solid. 400 MHz $^1$H-NMR (DMSO-$d_6$, ppm): 12.8-11.2 (m, 2H) 10.5-9.5 (br s, 1H) 7.86 (d, J=4.1 Hz, 1H) 7.53-7.41 (m, 1H) 7.24-7.14 (m, 1H) 4.72 (s, 1H) 1.71 (s, 3H) 1.50 (s, 3H). ESI-MS (m/z): 268 $[M+H]^+$ Example 2: (S)-2-(3-Hydroxy-pyridin-2-ylamino)-5,5-dimethyl-4,5-dihydro-thiazole-4-carboxylic Acid (5) and Corresponding Hydrochloride Salt (5a)

(a) (S)-2-(3-Hydroxy-pyridin-2-ylamino)-5,5-dimethyl-4,5-dihydro-thiazole-4-carboxylic Acid (5)

D-Penicillamine (80 mg, 0.54 mmol) was reacted with 2-chloro-oxazolo[4,5-b]pyridine hydrochloride (3) using procedure described for compound (4). The product was purified by reverse phase flash chromatography using gradient elution from $H_2O$ to $H_2O$/MeCN (40:60) to give (R)-2-(3-hydroxy-pyridin-2-ylamino)-5,5-dimethyl-4,5-dihydro-thiazole-4-carboxylic acid (5) (75 mg, 52% yield) as an off-white solid. 300 MHz $^1$H-NMR (CD$_3$OD, ppm): 7.96-7.82 (m, 1H) 7.38-7.25 (m, 1H) 7.21-7.08 (m, 1H) 4.66 (s, 1H) 1.83 (s, 3H) 1.62 (s, 3H). ESI-MS (m/z): 268 [M+H]$^+$. [α$_D^{20}$]: +137.1 (0.28, methanol).

(b) (S)-2-(3-Hydroxy-pyridin-2-ylamino)-5,5-dimethyl-4,5-dihydro-thiazole-4-carboxylic Acid Hydrochloride (5a)

(S)-2-(3-Hydroxy-pyridin-2-ylamino)-5,5-dimethyl-4,5-dihydro-thiazole-4-carboxylic acid (5) (70 mg, 0.26 mmol) was treated with 4N HCl in 1,4-dioxane in diethyl methanol using procedure described for compound (4a) to produce (S)-2-(3-hydroxy-pyridin-2-ylamino)-5,5-dimethyl-4,5-dihydro-thiazole-4-carboxylic acid hydrochloride (5a) (60 mg, 75% yield) as an off-white solid. 300 MHz $^1$H-NMR (DMSO-d$_6$, ppm): 10.8-8.6 (br s, 1H) 7.77-7.64 (m, 1H) 7.11-7.01 (m, 1H) 6.83 (dd, J=7.8, 4.6 Hz, 1H) 4.22 (s, 1H) 1.61 (s, 3H) 1.38 (s, 3H). ESI-MS (m/z): 268 [M+H]$^+$.

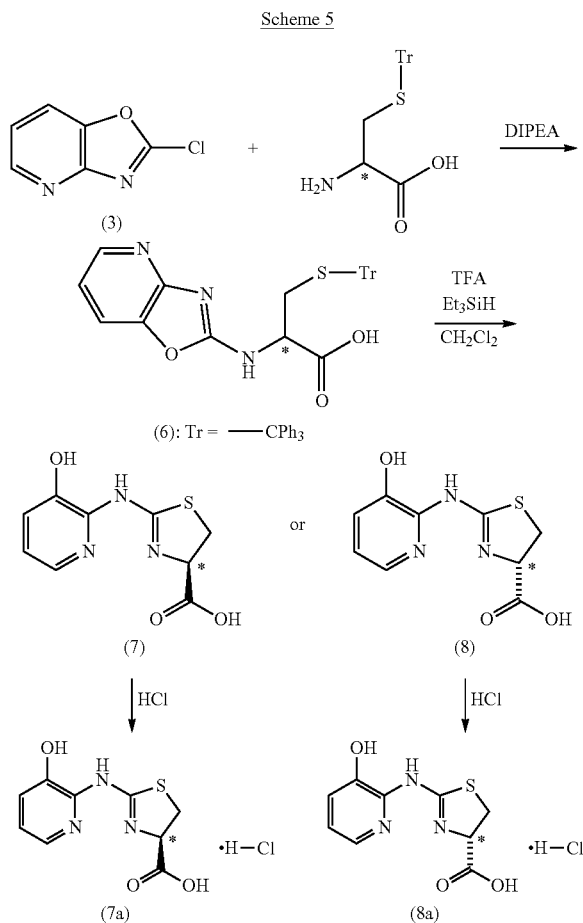

Example 3: (R)-2-((3-hydroxypyridin-2-yl)amino)-4,5-dihydrothiazole-4-carboxylic Acid Hydrochloride (7) and Corresponding Hydrochloride Salt (7a)

(a) N-(oxazolo[4,5-b]pyridin-2-yl)-S-trityl-L-cysteine (L-6)

A solution of 2-chloro-oxazolo[4,5-b]pyridine hydrochloride (3) (309 mg, 1.62 mmol), S-trityl-L-cysteine (590 mg, 1.62 mmol) and DIPEA (786 µL, 4.55 mmol) in THF/MeOH (4/10 mL) was stirred at room temperature for 20 h. After this time, the solvent was removed in vacuo. The remaining residue was suspended in water (30 mL), acidified to pH 3 with 5% KHSO$_4$ solution and extracted with in CH$_2$Cl$_2$ (3×15 mL). The combined organic extracts were washed with water (50 mL) and dried over solid anhydrous Na$_2$SO$_4$. After filtration and concentration, the residue was purified by flash chromatography (silica gel) using eluent from CH$_2$Cl$_2$ to CH$_2$Cl$_2$/MeOH (30:70) to give N-(benzo[d]oxazol-2-yl)-S-trityl-L-cysteine (L-6) (120 mg, 15% yield). 300 MHz $^1$H-NMR (DMSO-d$_6$, ppm): 8.2-8.0 (br s, 1H) 8.09 (dd, J=5.2, 1.4 Hz) 7.64 (dd, J=7.8, 1.4 Hz, 1H) 7.37-7.08 (m, 15H) 6.95 (dd, J=7.8, 5.2 Hz, 1H) 4.15-4.02 (m, 1H) 2.69-2.62 (m, 2H). ESI-MS (m/z): 482 [M+H]$^+$.

(b) (R)-2-((3-hydroxypyridin-2-yl)amino)-4,5-dihydrothiazole-4-carboxylic Acid and Corresponding Hydrochloride Salt (7)

To a solution of N-(oxazolo[4,5-b]pyridin-2-yl)-S-trityl-L-cysteine (L-6) (75 mg, 0.16 mmol) in CH$_2$Cl$_2$ (15 mL) at 0° C., Et$_3$SiH (82 µL, 0.51 mmol) was added, followed by TFA (120 µL, 1.56 mmol). The reaction was stirred for 30 min and then the volatiles were removed. The residue was triturated with diethyl ether, and solid (R)-2-((3-hydroxypyridin-2-yl)amino)-4,5-dihydrothiazole-4-carboxylic acid (7) was collected by filtration, and then dissolved in methanol and treated with 2N HCl/Et$_2$O solution (70 µL. 0.14 mmol). After removal of the volatile, the resultant residue was purified by reverse phase flash chromatography using gradient elution from H$_2$O to H$_2$O/MeCN (40:60) to give (R)-2-((3-hydroxypyridin-2-yl)amino)-4,5-dihydrothiazole-4-carboxylic acid hydrochloride (7a) (22 mg, 52% yield). 300 MHz 1H-NMR (CD$_3$OD, ppm): 7.91 (dd, J=4.9, 1.4 Hz, 1H) 7.32 (dd, J=8.0, 1.4 Hz, 1H) 7.15 (dd, J=8.0, 4.9 Hz, 1H) 4.96 (dd, J=9.0, 5.6 Hz, 1H) 3.86 (dd, J=11.4, 9.0 Hz, 1H) 3.75 (dd, J=11.4, 5.6 Hz, 1H). ESI-MS (m/z): 240 [M+H]$^+$.

Example 4: (S)-2-((3-hydroxypyridin-2-yl)amino)-4,5-dihydrothiazole-4-carboxylic Acid Hydrochloride (8) and Corresponding Hydrochloride Salt (8a)

(a) N-(oxazolo[4,5-b]pyridin-2-yl)-S-trityl-D-cysteine (D-6)

S-trityl-D-cysteine (716 mg, 1.97 mmol) was reacted with 2-chloro-oxazolo[4,5-b]pyridine hydrochloride (3) and DIPEA using procedure described for compound L-6 to produce N-(oxazolo[4,5-b]pyridin-2-yl)-S-trityl-D-cysteine (D-6) (370 mg, 39% yield). 300 MHz $^1$H-NMR (DMSO-d$_6$, ppm): 8.09 (dd, J=5.2, 1.4 Hz) 8.05 (br s, 1H) 7.65 (dd, J=7.8, 1.4 Hz, 1H) 7.34-7.12 (m, 15H) 6.95 (dd, J=7.8, 5.2 Hz, 1H) 4.17-4.02 (m, 1H) 2.70-2.61 (m, 2H). ESI-MS (m/z): 482 [M+H]$^+$.

(b) (S)-2-((3-hydroxypyridin-2-yl)amino)-4,5-dihydrothiazole-4-carboxylic Acid (8) and Corresponding Hydrochloride Salt (8a)

N-(oxazolo[4,5-b]pyridin-2-yl)-S-trityl-D-cysteine (D-6) (360 mg, 0.75 mmol) was reacted with TFA/Et$_3$SiH to obtain (S)-2-((3-hydroxypyridin-2-yl)amino)-4,5-dihydrothiazole-4-carboxylic acid (8), then treated with HCl/Et$_2$O solution to produce (S)-2-((3-hydroxypyridin-2-yl)amino)-4,5-dihydrothiazole-4-carboxylic acid hydrochloride (8a) (60 mg, 29% yield). 300 MHz $^1$H-NMR (CD$_3$OD, ppm): 7.96-7.90

(m, 1H) 7.40-7.32 (m, 1H) 7.19 (dd, J=8.1, 4.8 Hz, 1H) 5.25-5.11 (m, 1H) 4.00-3.89 (m, 1H), 3.79 (dd, J=11.6, 4.8 Hz, 1H). ESI-MS (m/z): 240 [M+H]$^+$.

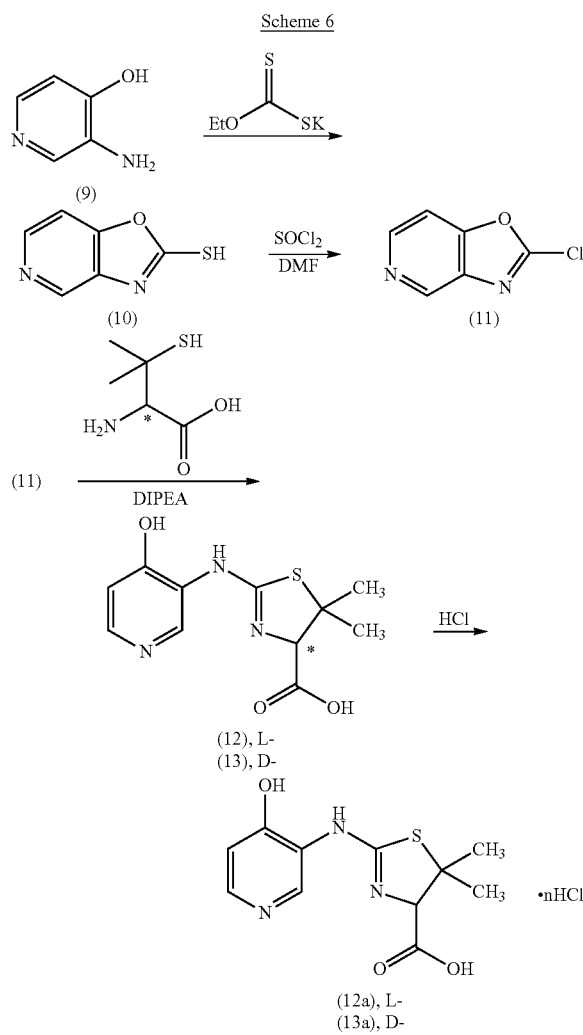

Example 5: (R)-2-((4-Hydroxypyridin-3-yl)amino)-5,5-dimethyl-4,5-dihydrothiazole-4-carboxylic Acid Hydrochloride (12) and Corresponding Hydrochloride Salt (12a)

(a) Oxazolo[4,5-c]pyridine-2-thiol (10)

A mixture of 3-amino-4-hydroxypyridine (9) (780 mg, 7.08 mmol) and potassium ethyl xanthate (2.27 g, 14.17 mmol) in ethanol (40 mL) was heated at reflux for 24 h. The solvent was removed in vacuo and water (30 mL) was added. The mixture was acidified with AcOH to pH 5. The resultant precipitate was filtered, washed with water (20 mL) and dried to afford oxazolo[4,5-c]pyridine-2-thiol (10) (770 mg, 71% yield). 300 MHz $^1$H-NMR (DMSO-d$_6$, ppm): 8.46 (s, 1H) 8.30 (d, J=6.0 Hz, 1H) 7.43 (d, J=6.0, 1H).

(b) 2-Chlorooxazolo[4,5-c]pyridine Hydrochloride (11)

A mixture of oxazolo[4,5-c]pyridine-2-thiol (10) (650 mg, 4.27 mmol), sulfuryl chloride (8 mL), and catalytic amount of DMF (25 μL) was stirred at 60° C. for 20 h. The mixture was cooled and the resulting crystals were filtered, washed with petroleum ether (20 mL), diethylether (20 mL) and dried to give 2-chlorooxazolo[4,5-c]pyridine hydrochloride (11) (660 mg, 99% yield), which was used in the next step without purification. 300 MHz $^1$H-NMR (DMSO-d$_6$, ppm): 8.78 (s, 1H) 8.71 (d, J=6.4 Hz, 1H) 8.01 (d, J=6.4, 1H).

(c) (R)-2-((4-Hydroxypyridin-3-yl)amino)-5,5-dimethyl-4,5-dihydrothiazole-4-carboxylic Acid (12)

A mixture of L-penicillamine (130 mg, 0.87 mmol), 2-chlorooxazolo[4,5-c]pyridine hydrochloride (11) (198 mg, 1.04 mmol), and Na$_2$CO$_3$ (554 mg, 5.23 mmol) in THF/MeOH (2/10 mL) was stirred at room temperature for 2 h. The solvents were then removed in vacuo. The residue was suspended in water (100 mL) and acidified to pH 3 with 5% KHSO$_4$ solution. The mixture was purified by reverse phase flash chromatography using gradient elution from H$_2$O to H$_2$O/MeCN (40:60) to give (R)-2-((4-hydroxypyridin-3-yl)amino)-5,5-dimethyl-4,5-dihydrothiazole-4-carboxylic acid (12) (80 mg, 34% yield). 300 MHz $^1$H-NMR (DMSO-d$_6$, ppm): 11.41 (br s, 1H) 8.82-8.69 (m, 1H) 7.61 (dd, J=7.0, 1.3 Hz, 1H) 6.19 (d, J=7.0, 1H) 4.49 (s, 1H) 1.62 (s, 1H) 1.38 (s, 1H). ESI-MS (m/z): 268 [M+H]$^+$.

(d) (R)-2-((4-Hydroxypyridin-3-yl)amino)-5,5-dimethyl-4,5-dihydrothiazole-4-carboxylic Acid Hydrochloride (12a)

(R)-2-((4-Hydroxypyridin-3-yl)amino)-5,5-dimethyl-4,5-dihydrothiazole-4-carboxylic acid (12) (77 mg, 0.29 mmol) was dissolved in methanol (3 mL) and 4N HCl in 1,4-dioxane (79 μL, 0.32 mmol) was added at 0° C. The mixture was stirred for 30 min and then the volatiles were removed in vacuo. The residue was treated with CH$_2$Cl$_2$, and the resultant precipitate was filtered to give (R)-2-((4-hydroxypyridin-3-yl)amino)-5,5-dimethyl-4,5-dihydrothiazole-4-carboxylic acid hydrochloride (12a) (82 mg, 94% yield). 300 MHz $^1$H-NMR (DMSO-d$_6$, ppm): 8.35-8.20 (m, 1H) 8.03-7.96 (m, 1H) 6.80-6.72 (m, 1H) 4.60 (s, 1H) 1.70 (s, 3H) 1.48 (s, 3H). ESI-MS (m/z): 268 [M+H]$^+$.

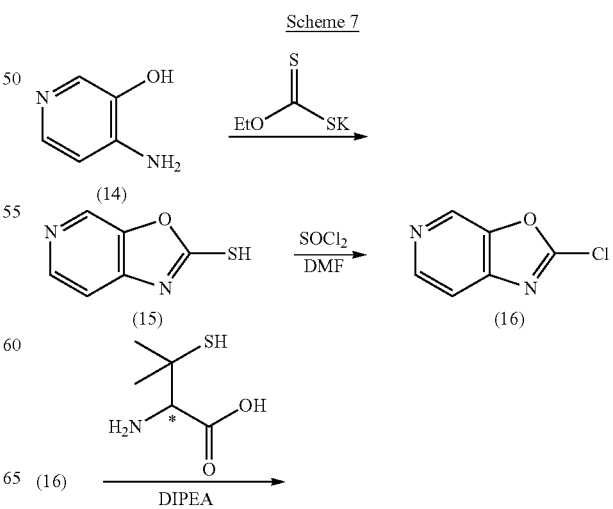

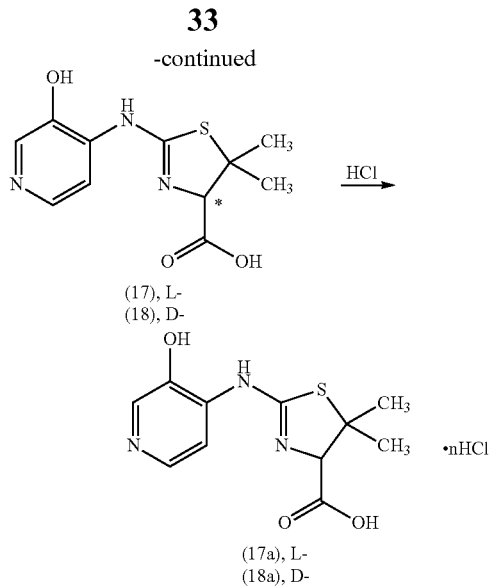

(17), L-
(18), D-

(17a), L-
(18a), D-

Example 6: (R)-2-((3-Hydroxypyridin-4-yl)amino)-5,5-dimethyl-4,5-dihydrothiazole-4-carboxylic Acid Hydrochloride (17) and Corresponding Hydrochloride Salt (17a)

(a) Oxazolo[5,4-c]pyridine-2-thiol (15)

4-Aminopyridin-3-ol (14) (1.00 g, 9.08 mmol) was reacted with potassium ethyl xanthate using procedure described for compound (10) to afford oxazolo[5,4-c]pyridine-2-thiol (15) (650 mg, 47% yield). 300 MHz 1H-NMR (DMSO-$d_6$, ppm): 8.64-8.61 (m, 1H) 8.30 (d, J=6.1 Hz, 1H) 7.40 (dd, J=6.1, 0.5 Hz, 1H).

(b) 2-Chlorooxazolo[5,4-c]pyridine Hydrochloride (16)

A mixture of oxazolo[5,4-c]pyridine-2-thiol (15) (560 mg, 3.68 mmol), thionyl chloride (12 mL), and catalytic amount of DMF (40 μL) was stirred at room temperature for 2 h. The volatiles were removed in vacuo. The residue was co-evaporated with toluene (3×20 mL), then triturated with another portion of toluene (15 mL). The resultant precipitate was filtered to give 2-chlorooxazolo[5,4-c]pyridine hydrochloride (16) (450 mg, 64% yield). 400 MHz $^1$H-NMR (DMSO-$d_6$, ppm): 9.00-8.99 (m, 1H) 8.61 (dd, J=6.3, 0.7 Hz, 1H) 7.68 (dd, J=6.3, 0.5 Hz, 1H).

(c) (R)-2-((3-Hydroxypyridin-4-yl)amino)-5,5-dimethyl-4,5-dihydrothiazole-4-carboxylic Acid (17)

L-Penicillamine (240 mg, 1.61 mmol) was reacted with 2-chlorooxazolo[5,4-c]pyridine hydrochloride (16) using procedure described for compound (12). The product was purified by reverse phase flash chromatography using gradient elution from H$_2$O to H$_2$O/MeCN (40:60) to give (R)-2-((3-hydroxypyridin-4-yl)amino)-5,5-dimethyl-4,5-dihydrothiazole-4-carboxylic acid (17) (90 mg, 26% yield). ESI-MS (m/z): 268 [M+H]$^+$.

(d) (R)-2-((3-Hydroxypyridin-4-yl)amino)-5,5-dimethyl-4,5-dihydrothiazole-4-carboxylic Acid Hydrochloride (17a)

(R)-2-((3-Hydroxypyridin-4-yl)amino)-5,5-dimethyl-4,5-dihydrothiazole-4-carboxylic acid (17) (85 mg, 0.32 mmol) was treated with 4N HCl/1,4-dioxane in methanol using procedure described for compound (12a) to produce (R)-2-((3-hydroxypyridin-4-yl)amino)-5,5-dimethyl-4,5-dihydrothiazole-4-carboxylic acid hydrochloride (17a) (88 mg, 91% yield). 300 MHz $^1$H-NMR (D$_2$O, ppm): 8.18 (d, J=1.0 Hz, 1H) 8.15 (dd, J=6.4, 1.0 Hz, 1H) 7.75 (d, J=6.4 Hz, 1H) 4.59 (s, 1H) 1.78 (s, 3H) 1.57 (s, 3H). ESI-MS (m/z): 268 [M+H]$^+$.

Example 7: (S)-2-((3-Hydroxypyridin-4-yl)amino)-5,5-dimethyl-4,5-dihydrothiazole-4-carboxylic Acid (18) and Corresponding Hydrochloride Salt (18a)

(a) (S)-2-((3-Hydroxypyridin-4-yl)amino)-5,5-dimethyl-4,5-dihydrothiazole-4-carboxylic Acid (18)

D-Penicillamine (280 mg, 1.88 mmol) was reacted with 2-chlorooxazolo[5,4-c]pyridine hydrochloride (16) using procedure described for compound (17). The product was purified by reverse phase flash chromatography using gradient elution from H$_2$O to H$_2$O/MeCN (40:60) to give (S)-2-((3-hydroxypyridin-4-yl)amino)-5,5-dimethyl-4,5-dihydrothiazole-4-carboxylic acid (18) (90 mg, 25% yield). 300 MHz $^1$H-NMR (DMSO-$d_6$, ppm): 8.03-8.01 (m, 1H) 7.87 (d, J=5.3 Hz, 1H) 7.41-7.20 (m, 1H) 4.44 (s, 1H) 1.64 (s, 3H) 1.41 (s, 1H). ESI-MS (m/z): 268 [M+H]$^+$.

(b) (S)-2-((3-Hydroxypyridin-4-yl)amino)-5,5-dimethyl-4,5-dihydrothiazole-4-carboxylic Acid Hydrochloride (18a)

(S)-2-((3-Hydroxypyridin-4-yl)amino)-5,5-dimethyl-4,5-dihydrothiazole-4-carboxylic acid (18) (88 mg, 0.33 mmol) was treated with 4N HCl/1,4-dioxane in methanol using procedure described for compound (17) to produce (S)-2-((3-hydroxypyridin-4-yl)amino)-5,5-dimethyl-4,5-dihydrothiazole-4-carboxylic acid hydrochloride (18a) (92 mg, 92% yield). 300 MHz $^1$H-NMR (D$_2$O, ppm): 8.21-8.12 (m, 2H) 7.84 (d, J=6.4 Hz, 1H) 4.60 (s, 1H) 1.78 (s, 3H) 1.57 (s, 3H). ESI-MS (m/z): 268 [M+H]$^+$.

Scheme 8

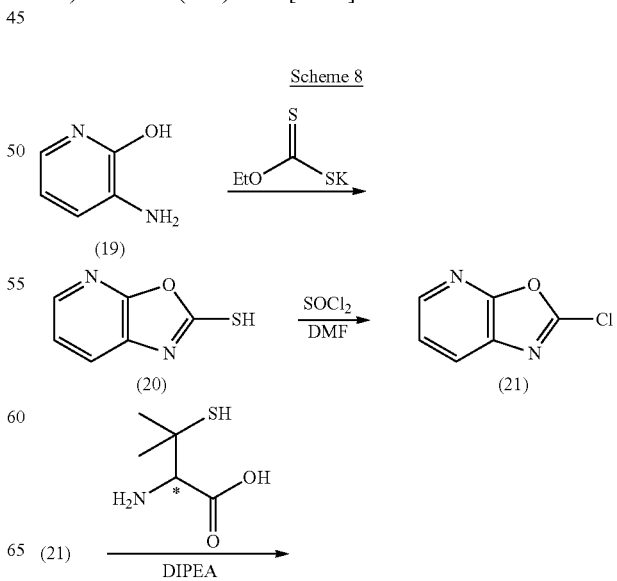

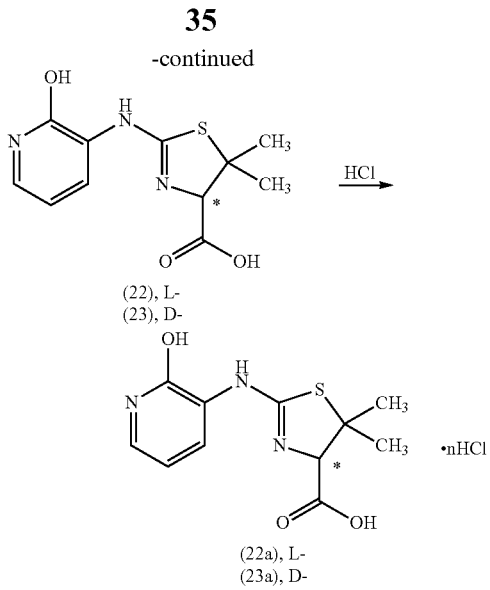

(22), L-
(23), D-

(22a), L-
(23a), D-

Example 8: (R)-2-((2-Hydroxypyridin-3-yl)amino)-5,5-dimethyl-4,5-dihydrothiazole-4-carboxylic Acid (22) and Corresponding Hydrochloride Salt (22a)

(a) 2-Chlorooxazolo[5,4-b]pyridine Hydrochloride (21)

Oxazolo[5,4-b]pyridine-2-thiol (20) (1.60 g, 10.51 mmol) was reacted with thionyl chloride using procedure described for compound (16) to afford 2-chlorooxazolo[5,4-b]pyridine hydrochloride (21) (1.60 g, 80% yield). 300 MHz $^1$H-NMR (DMSO-$d_6$, ppm): 8.40 (dd, J=5.0, 1.6 Hz, 1H) 8.25 (dd, J=7.9, 1.6 Hz, 1H) 7.54 (dd, J=7.9, 5.0 Hz, 1H).

(b) (R)-2-((2-Hydroxypyridin-3-yl)amino)-5,5-dimethyl-4,5-dihydrothiazole-4-carboxylic Acid (22)

A solution of 2-chlorooxazolo[5,4-b]pyridine hydrochloride (21) (300 mg, 1.30 mmol), L-penicillamine (300 mg, 2.01 mmol) and DIPEA (1.74 mL, 10.05 mmol) in THF/MeOH (4/12 mL) was stirred at room temperature for 2 h. The solvents were then removed in vacuo. The resultant residue was suspended in water (100 mL) and acidified to pH 3 with 5% KHSO$_4$ solution. The resultant precipitate was filtered, and purified by reverse phase flash chromatography using gradient elution from H$_2$O to H$_2$O/MeCN (20:80) to give (R)-2-((2-hydroxypyridin-3-yl)amino)-5,5-dimethyl-4,5-dihydrothiazole-4-carboxylic acid (22) (240 mg, 69% yield). 300 MHz $^1$H-NMR (DMSO-$d_6$, ppm): 11.77 (br s, 1H) 8.22-8.10 (m, 1H) 6.98 (dd, J=6.6, 1.7 Hz, 1H) 6.17 (dd, J=7.0, 6.7 Hz, 1H) 4.44 (s, 1H) 1.61 (s, 3H) 1.37 (s, 1H). ESI-MS (m/z): 268 [M+H]$^+$.

(c) (R)-2-((2-Hydroxypyridin-3-yl)amino)-5,5-dimethyl-4,5-dihydrothiazole-4-carboxylic Acid Hydrochloride (22a)

(R)-2-((2-Hydroxypyridin-3-yl)amino)-5,5-dimethyl-4,5-dihydrothiazole-4-carboxylic acid (22) (145 mg, 0.54 mmol) was treated with 4N HCl/1,4-dioxane in methanol using procedure described for compound (12a) to produce (R)-2-((2-hydroxypyridin-3-yl)amino)-5,5-dimethyl-4,5-dihydrothiazole-4-carboxylic acid hydrochloride (22a) (155 mg, 94% yield). 300 MHz $^1$H-NMR (DMSO-$d_6$, ppm): 12.6-12.2 (br s, 1H) 7.72-7.60 (m, 1H) 7.52-7.40 (m, 1H) 6.36-6.27 (m, 1H) 4.70 (s, 1H) 1.72 (s, 3H) 1.50 (s, 3H). ESI-MS (m/z): 268 [M+H]$^+$; melting point: 211-213° C.

Example 9: (S)-2-((2-Hydroxypyridin-3-yl)amino)-5,5-dimethyl-4,5-dihydrothiazole-4-carboxylic Acid (23) and Corresponding Hydrochloride Salt (23a)

(a) (S)-2-((2-Hydroxypyridin-3-yl)amino)-5,5-dimethyl-4,5-dihydrothiazole-4-carboxylic Acid (23)

D-Penicillamine (450 mg, 3.02 mmol) was reacted with 2-chlorooxazolo[5,4-b]pyridine hydrochloride (21) using procedure described for compound (22). The product was purified by reverse phase flash chromatography using gradient elution from H$_2$O to H$_2$O/MeCN (20:80) to give (S)-2-((2-hydroxypyridin-3-yl)amino)-5,5-dimethyl-4,5-dihydrothiazole-4-carboxylic acid (23) (420 mg, 94% yield). 300 MHz $^1$H-NMR (DMSO-$d_6$, ppm): 12.07 (br s, 1H) 8.00-7.87 (m, 1H) 7.27-7.15 (m, 1H) 6.28-6.20 (m, 1H) 4.58 (s, 1H) 1.66 (s, 3H) 1.43 (s, 1H). ESI-MS (m/z): 268 [M+H]$^+$.

(b) (S)-2-((2-Hydroxypyridin-3-yl)amino)-5,5-dimethyl-4,5-dihydrothiazole-4-carboxylic Acid Hydrochloride (23a)

(S)-2-((2-Hydroxypyridin-3-yl)amino)-5,5-dimethyl-4,5-dihydrothiazole-4-carboxylic acid (23) (350 mg, 1.31 mmol) was treated with 4N HCl/1,4-dioxane in methanol using procedure described for compound (12a) to produce (S)-2-((2-hydroxypyridin-3-yl)amino)-5,5-dimethyl-4,5-dihydrothiazole-4-carboxylic acid hydrochloride (23a) (300 mg, 75% yield). 300 MHz 1H-NMR (DMSO-$d_6$, ppm): 12.3-11.9 (br s, 1H) 8.02-7.80 (m, 1H) 7.31-7.15 (m, 1H) 6.31-6.18 (m, 1H) 4.59 (s, 1H) 1.66 (s, 3H) 1.44 (s, 3H). ESI-MS (m/z): 268 [M+H]$^+$.

Scheme 9

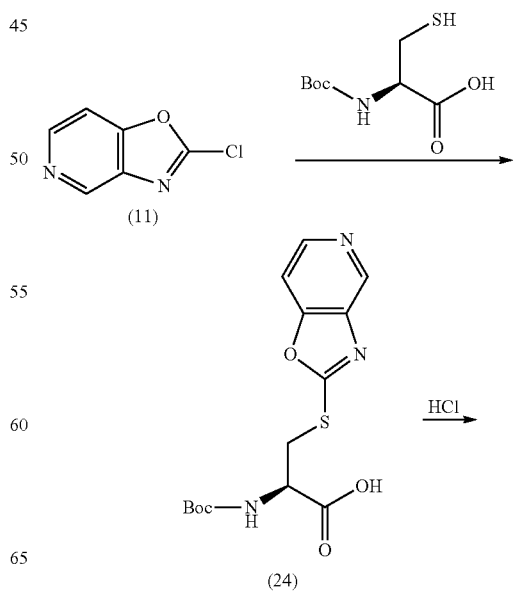

(11)

(24)

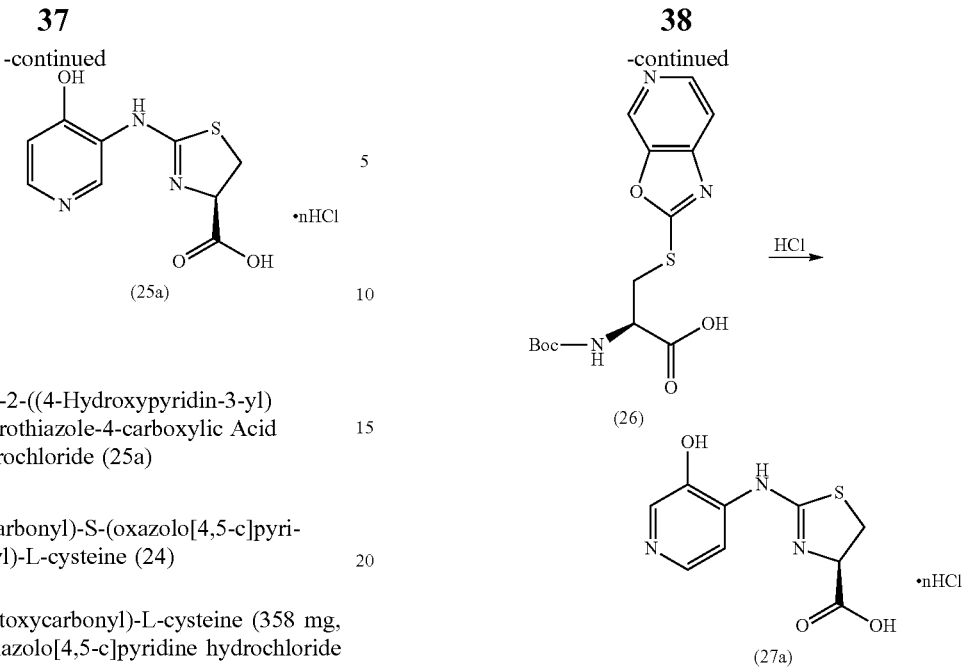

Example 10: (R)-2-((4-Hydroxypyridin-3-yl)amino)-4,5-dihydrothiazole-4-carboxylic Acid Hydrochloride (25a)

(a) N-(tert-Butoxycarbonyl)-S-(oxazolo[4,5-c]pyridin-2-yl)-L-cysteine (24)

A mixture of (tert-butoxycarbonyl)-L-cysteine (358 mg, 1.62 mmol), 2-chlorooxazolo[4,5-c]pyridine hydrochloride (11) (358 mg, 1.87 mmol) and $Na_2CO_3$ (857 mg, 8.09 mmol) in THF (15 mL) was stirred at room temperature for 2 h. The solvents were then removed in vacuo. The residue was purified by flash chromatography using gradient elution from $CH_2Cl_2$/MeOH (99:1) to $CH_2Cl_2$/MeOH (1:1) to give N-(tert-butoxycarbonyl)-S-(oxazolo[4,5-c]pyridin-2-yl)-L-cysteine (24) (148 mg, 27% yield). 300 MHz $^1$H-NMR ($CD_3OD$, ppm): 8.82-8.77 (m, 1H) 8.43 (dd, J=5.6, 1.2 Hz, 1H) 7.64 (dd, J=5.6, 1.1 Hz, 1H) 4.43 (dd, J=7.2, 4.4 Hz, 1H) 4.04 (dd, J=13.4, 4.4 Hz, 1H) 3.65 (dd, J=13.4, 7.2 Hz, 1H) 1.37 (s, 9H). ESI-MS (m/z): 340 [M+H]$^+$.

(b) (R)-2-((4-Hydroxypyridin-3-yl)amino)-4,5-dihydrothiazole-4-carboxylic Acid Hydrochloride (25a)

N-(tert-Butoxycarbonyl)-S-(oxazolo[4,5-c]pyridin-2-yl)-L-cysteine (24) (120 mg, 0.35 mmol) was suspended in 4N HCl/1,4-dioxane (10 mL) and stirred at room temperature for 3 hours. The volatiles were then removed and the residue was treated with diethyl ether (10 mL). The resultant precipitate was filtered and purified by reverse phase flash chromatography using gradient elution from $H_2O$ to $H_2O$/MeCN (75:25) to give (R)-2-((4-hydroxypyridin-3-yl)amino)-4,5-dihydrothiazole-4-carboxylic acid hydrochloride (25a) (45 mg, 46% yield). 300 MHz $^1$H-NMR ($D_2O$, ppm): 8.25 (d, J=1.6 Hz, 1H) 7.98 (dd, J=7.3, 1.6 Hz, 1H) 6.77 (d, J=7.3 Hz, 1H) 4.99-4.89 (m, 1H) 4.01 (dd, J=11.6, 9.1 Hz, 1H) 3.80 (dd, J=11.6, 4.5 Hz, 1H). ESI-MS (m/z): 240 [M+H]$^+$.

Scheme 10

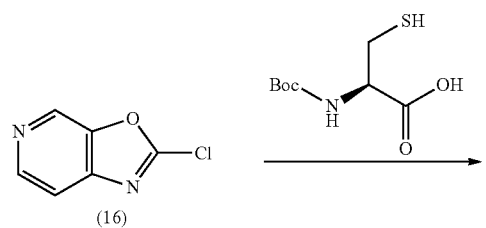

Example 11: (R)-2-(3-Hydroxy-pyridin-4-ylamino)-4,5-dihydro-thiazole-4-carboxylic Acid Hydrochloride (27a)

(a) N-(tert-Butoxycarbonyl)-S-(oxazolo[5,4-c]pyridin-2-yl)-L-cysteine (11c)

(tert-Butoxycarbonyl)-L-cysteine (143 mg, 0.52 mmol) and 2-chlorooxazolo[5,4-c]pyridine hydrochloride (16) (100 mg, 0.65 mmol) were suspended in THF (10 mL) and cooled to −20° C. After cooling, DIPEA (280 μL, 1.62 mmol) was added and the mixture was allowed to reach room temperature (2 hours). After this time, a 5% $KHSO_4$ Solution (7 mL) was added and the resulting suspension was extracted with EtOAc (3×20 mL). The combined organic extracts were washed with water (30 mL), then with brine (20 mL), and dried over solid anhydrous $Na_2SO_4$. The product was purified by flash chromatography using eluent from $CH_2Cl_2$ to $CH_2Cl_2$/MeOH (70:30) to give N-(tert-butoxycarbonyl)-S-(oxazolo[5,4-c]pyridin-2-yl)-L-cysteine (26) (120 mg, 68% yield). 300 MHz $^1$H-NMR (DMSO-$d_6$, ppm): 8.91 (d, J=0.9 Hz, 1H) 8.47 (d, J=5.3 Hz, 1H) 7.66 (dd, J=5.3, 0.9 Hz, 1H) 6.35-6.24 (m, 1H) 3.98-3.90 (m, 1H) 3.84 (dd, J=12.3, 5.0 Hz, 1H) 3.63 (dd, J=12.3, 6.2 Hz, 1H) 1.32 (s, 9H). ESI-MS (m/z): 340 [M+H]$^+$.

(b) (R)-2-(3-Hydroxy-pyridin-4-ylamino)-4,5-dihydro-thiazole-4-carboxylic Acid Hydrochloride (27a)

N-(tert-Butoxycarbonyl)-S-(oxazolo[5,4-c]pyridin-2-yl)-L-cysteine (26) (220 mg, 0.65 mmol) was treated with 4N HCl/1,4-dioxane using procedure described for compound (12a) to produce (R)-2-(3-hydroxy-pyridin-4-ylamino)-4,5-dihydro-thiazole-4-carboxylic acid hydrochloride (27a) (83 mg, 46% yield). 300 MHz $^1$H-NMR (DMSO-$d_6$, ppm): 11.5-9.3 (br s, 2H) 8.03 (s, 1H) 7.90 (d, J=5.3 Hz, 1H) 7.62-7.42 (m, 1H) 4.94-4.76 (m, 1H) 3.62 (dd, J=11.1, 8.6 Hz, 1H) 3.50 (dd, J=11.1, 5.9 Hz, 1H). ESI-MS (m/z): 240 [M+H]$^+$; melting point: 191° C. (dec.).

Example 12: Inhibition of SIN1-Mediated Peroxynitrite Oxidation of Luminol

Luminol-like compounds such as L-012 are chemiluminescent probes that are oxidized by the presence of ROS and RNS such as peroxynitrite. In this assay L-012 is oxidized by the addition of 3-morpholino-sydnonimine (SIN-1), a known peroxynitrite generator. The emitted luminescence is directly proportional to the concentration of SIN-1. The compounds were assessed for their ability to neutralize/scavenge/decompose peroxynitrite by blocking the increase of peroxynitrite induced chemiluminescence. Concentrations of compound producing 50% inhibition of the luminescence signal ($IC_{50}$ values) were calculated by testing the compounds at various concentrations of two parallel measurements. In the screening mode the concentration-response curve with $IC_{50}$ value determination was repeated if the lowest concentration of compound did not reach about 70 to 100% of control value.

L-012 Assay Protocol

Stock solution (10 mM) of compounds were prepared in 100% DMSO. From stock, test solutions of compounds at 100, 30, 10, 3 and 1 μM concentrations were prepared in phosphate-buffered solution (PBS, pH=8.5) (final concentration of compounds 10, 3, 1, 0.3, 0.1 μM). After initial measurement of compounds at 10 μM concentration, a concentration-response curve with $IC_{50}$ determination for active compounds was performed (when inhibition of peroxynitrite generation rate of compounds at 10 μM was more than 50% from control).

The following solutions were added to white polystyrene, non-sterile 96-well plate (Thermo Scientifi NUNC™ 96 MICROWELL™ White Polystyrene Plates#447796):

- 10 μL SIN-1 2 mM in 100% DMSO solution (SIN-1 final concentration 100 M, DMSO final volume—5%);
- 190 μL L012+/−test compound in phosphate-buffered solution (PBS, pH=8.5) (L012 final concentration 100 μM).

Luminescence signal was recorded by Hidex Sense multimodal microplate reader (Hidex) at 30° C. for 30 min, with a measurement every 60 sec and an integration time of isec.

L-012 Data Collection and Analysis $IC_{50}$ values were calculated using two different methods; first by measuring the slopes of the steepest linear portion of the kinetic profile during the first 5 min (as % from control) and secondly, by measuring the maximal luminescence at 30 min time point (as % from control). $IC_{50}$ values of the tested compounds were calculated using GraphPad Prism 5.0 software package.

Compounds with $IC_{50} > 10$ μM (in % PN gen, or in % luminol absorb. @ 30 min) are considered to be inactive in the present assays.

TABLE 1

Inhibition of Peroxynitrite generation from SIN1 and Inhibition of SIN1-luminol signal by compounds of the invention

| Cmpd # | Peroxynitrite gen (% control, 10 μM) | $IC_{50}$ (μM) (% PN gen) | $IC_{50}$ (μM) (% luminol absorb. @ 30 min) |
|---|---|---|---|
| resveratrol | 1 | 0.41 | 0.2 |
| 4a | 0 | 0.26 | 1.8 |
| 5a | 0 | 0.17 | 1.6 |
| 7a | 0 | 0.17 | 1.8 |
| 8a | 0 | 0.23 | 2.1 |
| 12a | 82 | >10 | >10 |
| 17a | 75 | >10 | >10 |
| 18a | 77 | >10 | >10 |
| 22a | 96 | >10 | >10 |
| 23a | 67 | >10 | >10 |
| 25a | 111 | >10 | >10 |
| 27a | 61 | >10 | >10 |

Example 13: Inhibition of Peroxynitrite Mediated Cytotoxicity

ATPlite is an Adenosine TriPhosphate monitoring system based on firefly luciferase. ATP monitoring was used as a measure of PC12 cell viability, as it is present in all metabolically active cells and its concentration very rapidly declines as cells undergo necrosis and apoptosis. ATPlite is based upon the production of light given off during the reaction of ATP & D-Luciferin in the presence of Luciferase. The emitted light is proportional to the ATP concentration. Compounds of the invention were assessed for their ability to inhibit SIN-1 induced cell toxicity. Inhibitory concentrations, $IC_{50}$ values, were calculated by testing compounds of the invention at various concentrations and averaging the $IC_{50}$ of two plates.

Cell Preparation

All cell work was carried out under the cell culture hood in a sterile environment. On Day 1, rat pheochromocytoma cells (PC12) cells were dissociated from T75 flasks with 0.25% trypsin/EDTA for approximately 2 minutes. Cells were harvested by adding 10 mL of F12K media to each flask and collecting cells into a sterile 15 mL conical tube. From this, 10 μL of cells were placed into 90 μL of trypan blue in a 1.5 mL microfuge tube. This was equal to a dilution factor of 10. The microfuge tube was mixed via vortex briefly, and 10 μL was added into one side of a hemacytometer. The cells were counted in the 4 large corner quadrants of the hemacytometer under the inverted microscope at 10× and the average of the 4 quadrants was calculated. Blue cells were not counted as these cells represented non-viable cells. The number of cells present in 1 mL of media was determined using the following equation: cells/mL=(#cells counted/#squares counted)×$10^4$× dilution factor. (For example: 2.5×$10^6$ cells/mL=(100 cells/4 squares)×10000×10). Harvested cells were diluted in F12K media containing high serum (10% horse serum, 5% fetal bovine serum, 1% penicillin streptomycin) so that there were 300,000 cells in 1 mL. From this, 100 μL of cells/media were added to a sterile, clear-bottom collagen-coated 96-well plate (30,000 cells/well). The cells were allowed to attach overnight at 37° C., 5% $CO_2$.

Inhibition of Peroxynitrite Mediated Cytotoxicity—Protocol

All cell work is carried out under the cell culture hood in a sterile environment. On Day 2, media was removed from each plate and replaced with 100 μl of F12K containing low serum (1% horse serum, 1% penicillin streptomycin). To test the concentration-response of compounds of the invention, serial dilutions of these compounds of 5 mM down to 0.02 mM were prepared in PBS. Each dilution (2 μl volume) was added to the appropriate wells in quadruplicate. Test compounds were incubated on the cells at 37° C. before adding 2 μL of 50 mM SIN-1. The cells were then incubated overnight at 37° C.

On Day 3, 10.25 mL of ATPlite buffer was added to 1 vial of lyophilized substrate solution (ATPlite 1 step luminescence ATP detection Assay system (Perkin Elmer, #6016731)). To each plate, 100 μl/well of lyophilized solution was added and mixed on an orbital plate shaker for 2 min at 250 rpm. The plate was read within 5 min the FlexStation3 in luminescence mode.

Cell Based Data Analysis.

Luminescence signal was recorded by the FlexStation3 and percent of control was calculated. The wells containing only cells were used to calculate 100% of control, wells containing only SIN-1 was used to calculate 0%. The remaining data was plotted as % of control by subtracting the average of the SIN-1 controls and dividing by the 100% control value.

Example 14: Nerve Growth Factor (NGF) or Interleukin 6 (IL6) Induced Pain Hypersensitivity Model All behavioral studies were conducted using male C57Bl6 (Taconic Laboratories) mice weighing between 20 and 25 grams. Mice were used in behavioral experiments starting one week after arrival. Animals were housed with a 12 h light/dark cycle and had food and water available ad libitum.

Mice were placed in acrylic boxes with wire mesh floors and allowed to habituate for 1 hr. After pretreatment mechanical thresholds were recorded, animals received intraplantar injections of NGF (50 ng, Millipore, Billerica, Mass.) or IL6 (0.1 ng, R&D Systems) in a volume of 25 μL sterile 0.9% saline. Calibrated Von Frey filaments (Stoelting) were used for mechanical stimulation of the plantar surface of the left hindpaw and withdrawal thresholds were calculated using the up-down method (Chaplan, et al., 1994, J. Neurosci. Methods 53:55-63). Paw withdrawal thresholds were measured at 1 hr, 3 hr, 24 hr, 48 h and 72 h post injection. Mouse grimace scale measurements were made from videos captured at 1 h, 3 h and 24 h after injection of compounds as described previously (Langford, et al., 2010, Nature Methods 7:447-449). A mouse model for 'hyperalgesic priming' originally developed by Levine and colleagues (for review see Reichling, et al., 2009, Trends Neurosci. 32:611-618) and adapted for mice (Asiedu, et al., 2011, J. Neurosci. 31:6646-6653) was used for the study. For assessment of hyperalgesic priming, animals were baselined for mechanical thresholds after recovery from NGF or IL6 mechanical hypersensitivity and subsequently injected in the left hindpaw with 100 ng of prostaglandin $E_2$ (PGE$_2$, Cayman Chemical, Ann Arbor, Mich., USA) in 25 μl sterile 0.9% NaCl. Following PGE$_2$ injection, paw withdrawal thresholds were again measured at 1 hr, 3 hr and 24 hr following the PGE$_2$ injection. Mouse grimace scale measurements were made from videos captured at 1 h, 3 h and 24 h after injection of compounds. AMPK activator dosing was done in a volume of 25 μL 0.9% sterile saline for intraplantar injections or in 0.5% hydroxypropyl methylcellulose plus 0.1% polysorbate-80 (both from Sigma, St. Louis, Mo., USA) in ultrapure $H_2O$ in a total volume of 200 μL by oral gavage.

The experimenters measuring mechanical withdrawal thresholds or scoring mouse facial expressions were always blinded to the experimental conditions. Mice were randomized to groups by a blinded experimenter and mice of individual groups were never housed together (e.g. home cages were always mixed between experimental groups).

Plantar Incision and Behavioral Testing:

Prior to surgery all animals were assessed for paw withdrawal thresholds. A mouse model of incisional pain was used for this study (Banik, et al., 2006, Anesthesiology 105:1246-1253). A 5 mm longitudinal incision was made with a number 11 blade through skin, fascia and muscle of the plantar aspect of the hindpaw in isoflurane-anesthetized rats. Sham controls underwent the same procedure but without the incision. The skin was apposed with 2 sutures of 5 mm silk. Animals received intraplantar injection of resveratrol or vehicle around the incision at times indicated after incision. Animals were allowed to recover for 24 h and then paw withdrawal thresholds were measured at 24 h, 48 h, 72 h, and 5 d, 7 d, 9 d, 11 d, and 13 d post-surgery. Grimace scale measurements were made at 24 h and 48 h after incision from videos captured at those time points by a blinded observer. For hyperalgesic priming experiments, the animals received an intraplantar injection of PGE2 (100 ng/25 μl) 28 days following incision or sham procedures. The paw withdrawal thresholds were again measured at 1 h, 3 h and 24 h following the PGE2 injection. Grimace scale measurements were also done at these time points from videos captured and scored by blinded observers.

Example 15: Mouse Spared Nerve Injury (SNI) Model of Neuropathic Pain Model

Neuropathic Pain Surgery and Behavioral Testing:

Male mice (20-25 g) or male Sprague Dawley rats (250-300 g) were used. All animal procedures were approved by the Institutional Animal Care and Use Committee of The University of Texas at Dallas and were in accordance with International Association for the Study of Pain guidelines. Prior to surgery all animals were assessed for mechanical withdrawal thresholds (Chaplan, et al., 1994, J. Neurosci. Methods 53:55-63). During surgery animals are anesthetized with isoflurane gas anesthesia and kept on a warming pad during the surgery. Mice and rats are allowed to recover in a warmed cage for an hour after surgery. Antibiotics are administered to all animals after surgery to avoid infection. Spared nerve injury (SNI) was performed on the mice as described previously (Bourquin, et al., 2006, Pain 122:14 e11-14). The sciatic nerve of these mice is exposed at mid-thigh level and the common peroneal and tibial branches of the nerve are isolated, ligated and cut. The sural nerve is left intact. The overlying muscle is then closed and the skin is sutured closed. Spinal nerve ligation (SNL) was done on rats by tight ligation of the L5 and L6 spinal nerves as described by Kim & Chung, 1992, Pain 50:355-363.

Here the skin above the spinal column is incised and the L5 and L6 DRGs are exposed to reveal the spinal nerves. The spinal nerves are ligated and cut and the skin is then closed. Sham control animals underwent the same surgery and handling as the experimental animals but without the SNL or SNI. All animals were allowed to recover for 14 days and all testing commenced day 14 day post-surgery. Following nerve injury, only animals that developed paw withdrawal thresholds less than Ig for SNI and less than 4.7 g for SNL by day 14 post-surgery were used. Animals were placed in acrylic boxes with wire mesh floors and allowed to habituate for 1 hr. Pre-drug mechanical thresholds were recorded and the animals received intraperitoneal or oral gavage administration of AMPK activating test compounds or vehicle. Calibrated von Frey filaments (Stoelting, Wood Dale, Ill.) were used for mechanical stimulation of the plantar surface of the left hindpaw and withdrawal thresholds were calculated using the up-down method (Chaplan, et al., 1994, J. Neurosci. Methods 53:55-63).

Example 16: Effect of Compounds of the Invention on Capsaicin-Induced Hyperalgesia Rats were administered compounds of the invention prior to an intra-plantar administration of capsaicin, and withdrawal latencies were measured. Compounds of the invention can prevent the development of hyperalgesic pain states produced by capsaicin, a model of hyperalgesia well known to those skilled in the art.

Example 17: Effect of Compounds of the Invention on Incisional Hyperalgesia (Prophylaxis)

Rats were administered compounds of the invention prior to an intra-plantar incision. Vehicle, a reference compound (e.g., indomethacin, celecoxib, naproxen), or compounds of this invention were administered at the conclusion of a surgical incision and latency values were measured 24 h later (0 timepoint) and 30 min and 60 min thereafter. Determination of latencies was subsequently conducted 48 h and 72 h in the same manner. Compounds of the invention can prevent hyperalgesia due to a (surgical) incision.

Example 18: Effect of Compounds of the Invention on Incisional Hyperalgesia (Reversal)

Rats were administered compounds of the invention after an intra-plantar incision (2 h, 4 h, 6 h, 8 h, 12 h, 24 h). Vehicle, a reference compound (e.g., indomethacin, celecoxib, naproxen), or compounds of this invention were administered at these times. Determination of latencies was conducted at 30 min, 60 min, 2 h, 4 h, 6 h, 8 h and 12 h after administration. Compounds of the invention can reverse hyperalgesia due to a (surgical) incision.

Example 19: Effect of Compounds of the Invention on SIN1-Induced Hyperalgesia SIN1 releases peroxynitrite. Vehicle or compounds of the invention were administered before the an intraplantar dose of intravenous of SIN1 (e.g., 1 mg/kg). Latency was measured 2 h later. A second dose of SIN1 (1 mg/kg) was administered 30 min after the first test period and latency was again measured 2 h later. SIN1 was again administered 30 min and latency was again measured 2 h later. Compounds of the invention can block the development of hyperalgesia caused by (repeated dosing of) SIN-1, a known generator of peroxynitrite.

Example 20: Effect of Compounds of the Invention on Freund's Complete Adjuvant Model of Hyperalgesia Freund's complete adjuvant (FCA) intraplantar model of inflammatory pain produces behaviors similar to those observed in patients and has been widely used to assess novel pharmacological treatments (Lam, et al., 2008, J. Ethnopharmacol. 120:44-50).

In this assay, intraplantar injection of CFA was performed under 2.5-4.0% isoflurane/$O_2$ anesthesia, delivered via nose cone. After induction of anesthesia, the injection site was prepared in a sterile manner and 100 µL of a 50% suspension of FCA injected. After injection, animals were weighed and allowed to recover before being returned to their home cages.

Paw withdrawal latency to a thermal stimulus was assessed using a radiant heat source (Ugo Basile, Italy) aimed at the plantar surface of the left hind paw (Hargreaves test; Hargreaves, et al., 1988, Pain 32:77-88). A cut-off latency of 40 sec was set to avoid tissue damage. Paw withdrawal thresholds to a non-noxious tactile stimulus was assessed using an electronic von Frey apparatus that presented an increasing mechanical force to the plantar surface of the hind paw. Paw volume was measured by displacement of water and assuming a tissue density equal to that of water. Baseline latencies, thresholds and volume were taken prior to FCA injection and re-assessed 24-72 h later. The positive control was celecoxib (TRC, Montreal), and the negative control was vehicle (0.5% methyl cellulose, in phosphate buffered saline). Compounds of the invention were administered (25 mg/kg, i.v.; or 3-100 mg/kg, p.o.) either once immediately prior to FCA (preemptive) or 24-72 hours post-FCA (curative).

Paw volume was assessed 24-72 h post-dosing. Compounds of the invention were administered curatively, with behavior or paw volume was assessed 30-180 min post-dosing. Celecoxib (30 mg/kg p.o.) served as the positive control. Intraplantar injection of 100 µL of FCA into the hind paw resulted in the development of thermal hyperalgesia, tactile allodynia (as assessed by electronic von Frey) and edema as indicated by a decreased latency to a noxious thermal stimulus, decreased threshold to a non-noxious tactile stimulus and increase in paw volume. Compounds of the invention administered preemptively prevented the development of thermal hyperalgesia and tactile allodynia.

Intraplantar injection of 100 µL of FCA into the hind paw resulted in the development of thermal hyperalgesia, tactile allodynia (as assessed by von Frey stimuli) and edema as indicated by a decreased latency to a noxious thermal stimulus, decreased threshold to a non-noxious tactile stimulus and increase in paw volume. Compounds of the invention administered preemptively prevented the development of thermal hyperalgesia and tactile allodynia.

Example 21: Effect of Compounds of the Invention on Hyperalgesia and Edema Induced by Intraplanar Carrageenan The intraplantar carrageenan model of acute inflammatory pain in the rat results in behaviors similar to that observed in patients and has been widely used to assess novel pharmacological treatments (Whiteside, et al., 2005, J. Pharmacol. Exp. Ther. 314:1234-1240).

For this assay, paw withdrawal latency to a thermal stimulus was assessed using a radiant heat source (Ugo Basile, Italy) aimed at the plantar surface of the left hind paw (Hargreaves test). A cut-off latency of 40 sec is set to avoid tissue damage. Paw volume was measured by displacement of water and assuming a tissue density equal to that of water. Baseline latencies were taken prior to carrageenan administration and re-assessed 4 h later. Compounds of the invention or vehicle were administered (10 and 30 mg/kg, p.o.) 3 h after carrageenan (curative) and behavior assessed 1 h later. Additionally, compounds of the invention were administered 15 minutes prior to carrageenan (preemptive) and behavior assessed 4 h post carrageenan.

Indomethacin (positive control, 30 mg/kg p.o.) was administered prior to carrageenan and behavior assessed 4 h post-carrageenan.

Intraplantar injection of carrageenan was performed under 2.5-4.0% isoflurane/$O_2$ anesthesia, delivered via nose cone. After induction of anesthesia, the injection site was prepared in a sterile manner and 50 μL of a 2% λ-carrageenan was injected. After injection, animals were weighed and allowed to recover before being returned to their home cages.

The positive control was indomethacin (Sigma, St. Louis), and the negative control was vehicle (0.5% methyl cellulose). Male Sprague-Dawley Rats (Harlan, Il) were 250-300 g at time of dosing. The Hargreaves apparatus was obtained from Ugo Basile, Italy, and the λ-carrageenan was obtained from Sigma, St. Louis.

Intraplantar injection of 50 μL of carrageenan into the hind paw resulted in the development of thermal hyperalgesia and edema as indicated by a decreased latency to a noxious thermal stimulus and increase in paw volume.

Compounds of the invention can significantly prevent either carrageenan-induced edema or thermal hyperalgesia. When dosed preemptively indomethacin (30 mg/kg p.o.), the positive control, produced a statistically significant prevention of both thermal hyperalgesia and edema.

Example 22: Effect of Compounds of the Invention on Allodynia in the Rat Spinal Nerve Ligation (SNL) Model The spinal nerve ligation (SNL) model of neuropathic pain in the rat results in behaviors similar to that observed in patients (Kim & Chung, 1992, Pain 50(3):355-63) and has been widely used to assess novel pharmacological treatments (Sindrup & Jensen, 1999, Pain 83(3):389-400). Compounds of the invention were evaluated for its ability to reverse or prevent development of tactile allodynia in a rat model of neuropathic pain.

The positive control was gabapentin (Toronto Research Chemicals, Canada). The negative control was vehicle (0.5% methyl cellulose; 2-hydroxy-propyl-beta-cyclodextrin). Male Sprague-Dawley Rats (Harlan, 11) were 250-300 g at time of dosing. Von Frey filaments were obtained from Stoelting, Ill., and 7-0 silk, 4-0 vicryl sutures were obtained from Ethicon, N.J.

The surgical procedure was performed under 2.5-4.0% isoflurane/$O_2$ anesthesia, delivered via nose cone, and anesthesia was maintained for the duration of the surgery. After induction of anesthesia, the incision site was shaved and prepared in a sterile manner. A midline incision was performed, the LS transverse process removed and the LS spinal nerves tightly ligated with 7-0 silk suture material. The wound was closed in layers with 4-0 vicryl. Sham-operated control rats underwent the identical procedure however, the spinal nerve was not manipulated or ligated. After surgery, animals were weighed and allowed to recover before being returned to their home cages.

The effect of compounds of the invention on nerve injury induced tactile allodynia was investigated using von Frey filaments 1-3 weeks after tight ligation of the LS spinal nerve. Tactile thresholds were assessed using a series of calibrated von Frey monofilaments (Stoelting, Wood Dale, Ill.). Assessment of tactile allodynia was measured as the hind paw-withdrawal threshold that produced a 50% likelihood of a withdrawal using the up-down method. Thresholds were evaluated before surgery, and they were reassessed 1-3 weeks after SNL surgery. Rats were administered either a single acute dose of test article (30 mg/kg) on the day of surgery, QD (10 and 50 mg/kg) on days 1-5 post-surgery or QD (30 mg/kg) on days 1-5 post-surgery. Tactile thresholds were again assessed either 1 and 3 h, 3 and 5 h or once weekly after administration. Vehicle treated animals were included and gabapentin (100 mg/kg, i.p.) was used as the positive control. The number of animals per group was 8.

Spinal nerve ligation resulted in the development of tactile allodynia as indicated by a decreased paw withdrawal threshold to a non-noxious tactile mechanical stimulus, 3 to 4 weeks post-surgery. Using non-fasted animals, compounds of the invention can produce a statistically significant difference from vehicle treated animals. In separate experiments, gabapentin (100 mg/kg i.p.), the positive control, consistently produced a statistically significant reversal of allodynia.

Example 23: Effect of Compounds of the Invention on Latency to Fall from an Accelerating Rotarod Assay of Ataxia Ataxia is a common clinical problem with CNS-active compounds and can often confound interpretation of efficacy in preclinical pain models. The rotarod assay of ataxia has been widely used to assess the side-effect liability of novel pharmacological treatments (Jones & Roberts, 1968, J. Pharm. Pharmacol. 20:302-04).

The effect of compounds of the invention to impact latency to fall in an accelerating rotarod assay of ataxia in rats was evaluated. The positive control was haloperidol (Sigma, St. Louis), and the negative control was vehicle (which was hydroxypropylmethyl-cellulose and 15% DMA, 65% PEG300, and 20% D5W for haloperidol).

Male Sprague-Dawley Rats (Harlan, Ill.) were 250-300 g at time of dosing. Rotarod was obtained from IITC, CA. To examine the potential effects of compounds of the invention on motor performance, rats were tested on an accelerating rotarod (IITC, Ca). In this assay, rats were placed on the rotarod with the speed set to accelerate from 4 to 40 rpm over 300 sec. The maximum time spent on the rotarod was set at 300 seconds. Rats received two timed training trials (averaged to give the reported baseline) on the first day, then 24 h later rats were administered compound of the invention (30, 100 and 300 mg/kg, p.o.), haloperidol (3 mg/kg, p.o.) or vehicle. Latency to fall was assessed 1 h post-drug administration corresponding approximately to the $T_{max}$ for compounds of the invention when given orally to rats.

Latency to fall increased in all groups between baseline and post-drug effects; performance improves with repeated runs on the rotarod. A compound of the invention (30, 100 and 300 mg/kg, p.o.) did not significantly decrease latency to fall in the rotarod assay at 1 h post-dosing as compared to vehicle treated animals. In contrast, haloperidol (3 mg/kg, p.o.), the positive control, resulted in significant motor deficits 1 h post-administration.

ENUMERATED EMBODIMENTS

The following exemplary embodiments are provided, the numbering of which is not to be construed as designating levels of importance:

Embodiment 1 provides a compound of formula (I), or a salt, solvate, enantiomer, diastereoisomer or tautomer thereof:

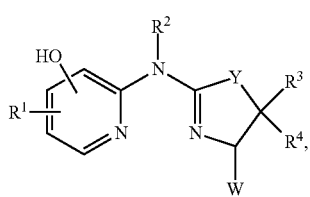

(I)

wherein:

Y is selected from the group consisting of S, O, NH, NR, and $CH_2$;

$R^1$ is selected from the group consisting of H, $C_1$-$C_6$ alkyl, $C_3$-$C_8$ cycloalkyl, $C_1$-$C_6$ alkenyl, $C_1$-$C_6$ alkynyl, aryl, arylalkyl, heteroarylalkyl, and heteroaryl, wherein the alkyl, cycloalkyl, alkenyl, alkynyl, aryl, arylalkyl, heteroarylalkyl, or heteroaryl group is independently optionally substituted;

$R^2$ is selected from the group consisting of H, —C(=O)H, —C(=O)—R, and —CH$_2$—OR;

$R^3$ and $R^4$ are independently selected from the group consisting of H and optionally substituted $C_1$-$C_6$ alkyl, or $R^3$ and $R^4$ can combine to form $C_1$-$C_6$ alkylene;

W is selected from the group consisting of H, $C_1$-$C_6$ alkyl, $C_3$-$C_8$ cycloalkyl, $C_1$-$C_6$ alkoxy, $C_1$-$C_6$ hydroxyalkyl, —CHO, —C(=O)OR, —C(=O)NRR, cyano, hydroxy, aryl, and heteroaryl, wherein the alkyl, alkoxy, cycloalkyl, aryl, or heteroaryl group is independently optionally substituted, and wherein each occurrence of R is independently H, $C_1$-$C_6$ alkyl, and $C_3$-$C_8$ cycloalkyl; and each occurrence of R is independently selected from the group consisting of $C_1$-$C_6$ alkyl and $C_3$-$C_8$ cycloalkyl.

Embodiment 2 provides the compound of embodiment 1, which is a compound of formula (Ia):

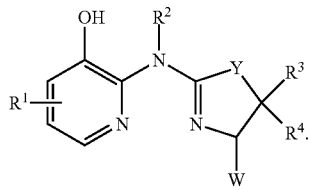

(Ia)

Embodiment 3 provides the compound of any one of embodiments 1-2, wherein $R^2$ is H.

Embodiment 4 provides the compound of any one of embodiments 1-3, wherein Y=S.

Embodiment 5 provides the compound of any one of embodiments 1-4, wherein W is selected from the group consisting of H, $C_1$-$C_6$ hydroxyalkyl, —CHO, —C(=O)OR, and —C(=O)NRR, wherein the alkyl, alkoxy, cycloalkyl, aryl, or heteroaryl group is independently optionally substituted and wherein each occurrence of R is independently H, $C_1$-$C_6$ alkyl, and $C_3$-$C_8$ cycloalkyl.

Embodiment 6 provides the compound of any one of embodiments 1-5, wherein $R^3$ and $R^4$ are independently selected from the group consisting of H and $C_1$-$C_6$ alkyl.

Embodiment 7 provides the compound of any of embodiments 1-6, which is selected from the group consisting of: (R)-2-(3-Hydroxy-pyridin-2-ylamino)-5,5-dimethyl-4,5-dihydro-thiazole-4-carboxylic acid; (S)-2-(3-Hydroxy-pyridin-2-ylamino)-5,5-dimethyl-4,5-dihydro-thiazole-4-carboxylic acid; (R)-2-((3-hydroxypyridin-2-yl)amino)-4,5-dihydrothiazole-4-carboxylic acid; (S)-2-((3-hydroxypyridin-2-yl)amino)-4,5-dihydrothiazole-4-carboxylic acid; and a salt, solvate, enantiomer, diastereoisomer or tautomer thereof.

Embodiment 8 provides a pharmaceutical composition comprising the compound of any one of embodiments 1-6.

Embodiment 9 provides a pharmaceutical composition comprising the compound of embodiments 1-8.

Embodiment 10 provides a method of preventing, reducing, or alleviating pain in a mammal, the method comprising administering a therapeutically effective amount of the compound of any one of embodiments 1-7 to the mammal.

Embodiment 11 provides the method of embodiment 10, wherein the administration is oral, parenteral, nasal, inhalational, intravenous, subcutaneous, transdermal, or enteral.

Embodiment 12 provides the method of any one of embodiments 10-11, wherein the mammal is a human.

Embodiment 13 provides the method of any one of embodiments 10-12, wherein the pain is spontaneous pain.

Embodiment 14 provides the method of any one of embodiments 10-12, wherein the pain is hyperalgesia.

Embodiment 15 provides the method of any one of embodiments 10-12, wherein the pain is allodynia.

Embodiment 16 provides the method of any one of embodiments 10-12, wherein the pain arises from a surgical procedure.

Embodiment 17 provides the method of embodiment 16, wherein the surgical procedure comprises third molar extraction, dental implants, lingual hernia repair, cholecystectomy, breast augmentation, abdominoplasty, vasectomy, hysterectomy, pacemaker implantation, and/or laparoscopic techniques.

Embodiment 18 provides the method of any one of embodiments 10-15, wherein the pain arises from trauma, sprains, broken bones, bruises, cuts, and/or burns.

Embodiment 19 provides the method of any one of embodiments 10-15 or 18, wherein the pain is neuropathic pain.

Embodiment 20 provides the method of any one of embodiments 10-15 or 18, wherein the pain is painful diabetic neuropathy.

Embodiment 21 provides the method of any one of embodiments 10-15 or 18, wherein the pain is chronic pain.

Embodiment 22 provides the method of any one of embodiments 10-15, wherein the pain arises from cancers, diabetes, Parkinson's Disease, Alzheimer's Disease, Amyotrophic Lateral Sclerosis, Multiple Sclerosis, and/or peripheral and/or central neuropathies.

Embodiment 23 provides the method of any one of embodiments 10-15, wherein the pain is caused by an inflammatory disease.

Embodiment 24 provides the method of embodiment 23, wherein the inflammatory disease comprises rheumatoid arthritis, osteoarthritis, lupus, inflammatory bowel syndrome, vulvodynia, and/or Sjorgen's disease.

Embodiment 25 provides the method of any one of embodiments 10-15, wherein the pain is caused by cancer chemotherapy, cancer radiation treatment, stroke, and/or myocardial infarct.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound of formula (Ia), or a salt, enantiomer, diastereoisomer, or tautomer thereof:

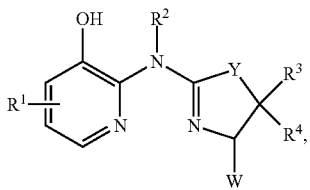

(Ia)

wherein:

Y is S;

$R^1$ is selected from the group consisting of H, $C_1$-$C_6$ alkyl, $C_3$-$C_8$ cycloalkyl, $C_1$-$C_6$ alkenyl, $C_1$-$C_6$ alkynyl, aryl, and arylalkyl, wherein the aryl or arylalkyl group is independently optionally substituted with 1 to 5 substituents selected from the group consisting of $C_{1-6}$ alkyl, —OH, $C_{1-6}$ alkoxy, halogen, amino, acetamido, and nitro;

$R^2$ is selected from the group consisting of H, —C(=O)H, —C(=O)—R, and —$CH_2$—OR;

$R^3$ and $R^4$ are independently selected from the group consisting of H and $C_1$-$C_6$ alkyl, or $R^3$ and $R^4$ can combine to form a $C_1$-$C_6$ alkylene;

W is selected from the group consisting of H, $C_1$-$C_6$ alkyl, $C_3$-$C_8$ cycloalkyl, $C_1$-$C_6$ alkoxy, $C_1$-$C_6$ hydroxyalkyl, —CHO, —C(=O)OR, —C(=O)NRR, cyano, hydroxy, and aryl, wherein the aryl group is optionally substituted with 1 to 5 substituents selected from the group consisting of $C_{1-6}$ alkyl, —OH, $C_{1-6}$ alkoxy, halogen, amino, acetamido, and nitro; and each occurrence of R is independently H, $C_1$-$C_6$ alkyl, or $C_3$-$C_8$ cycloalkyl.

2. The compound of claim 1, wherein $R^2$ is H.

3. The compound of claim 1, wherein W is selected from the group consisting of H, $C_1$-$C_6$ hydroxyalkyl, —CHO, —C(=O)OR, and —C(=O)NRR.

4. The compound of claim 3, wherein $R^3$ and $R^4$ are independently selected from the group consisting of H and $C_1$-$C_6$ alkyl.

5. A compound selected from the group consisting of:
(R)-2-(3-Hydroxy-pyridin-2-ylamino)-5,5-dimethyl-4,5-dihydro-thiazole-4-carboxylic acid;
(S)-2-(3-Hydroxy-pyridin-2-ylamino)-5,5-dimethyl-4,5-dihydro-thiazole-4-carboxylic acid;
(R)-2-((3-hydroxypyridin-2-yl)amino)-4,5-dihydrothiazole-4-carboxylic acid; and
(S)-2-((3-hydroxypyridin-2-yl)amino)-4,5-dihydrothiazole-4-carboxylic acid.

6. A pharmaceutical composition comprising the compound of claim 1 and at least one pharmaceutically acceptable carrier.

7. A pharmaceutical composition comprising the compound of claim 5 and at least one pharmaceutically acceptable carrier.

* * * * *